(12) United States Patent
Wagner et al.

(10) Patent No.: US 9,512,275 B2
(45) Date of Patent: Dec. 6, 2016

(54) LOW VISCOSITY POLYORGANOSILOXANES COMPRISING QUATERNARY AMMONIUM GROUPS, METHODS FOR THE PRODUCTION AND THE USE THEREOF (II)

(71) Applicant: Momentive Performance Materials GmbH, Leverkusen (DE)

(72) Inventors: Roland Wagner, Bonn (DE); Karl-Heinz Stachulla, Leverkusen (DE); Karl-Heinz Sockel, Leverkusen (DE); Sigfredo Gonzales, Danbury, CT (US); Anne Dussaud, Tarrytown, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 168 days.

(21) Appl. No.: 14/389,195

(22) PCT Filed: Mar. 26, 2013

(86) PCT No.: PCT/US2013/033816
§ 371 (c)(1),
(2) Date: Sep. 29, 2014

(87) PCT Pub. No.: WO2013/148635
PCT Pub. Date: Oct. 3, 2013

(65) Prior Publication Data
US 2015/0056155 A1    Feb. 26, 2015

Related U.S. Application Data

(60) Provisional application No. 61/617,180, filed on Mar. 29, 2012.

(51) Int. Cl.
| | |
|---|---|
| *C08G 77/26* | (2006.01) |
| *C08L 83/10* | (2006.01) |
| *D06M 13/46* | (2006.01) |
| *D06M 15/643* | (2006.01) |
| *A61Q 5/12* | (2006.01) |
| *A61K 8/898* | (2006.01) |
| *A61Q 5/02* | (2006.01) |
| *A61Q 5/06* | (2006.01) |
| *C08G 77/06* | (2006.01) |
| *C09D 183/08* | (2006.01) |
| *C11D 3/00* | (2006.01) |
| *C11D 3/37* | (2006.01) |
| *C11D 11/00* | (2006.01) |
| *D06M 15/65* | (2006.01) |
| *A61Q 19/00* | (2006.01) |
| *C08G 77/14* | (2006.01) |
| *C08G 77/388* | (2006.01) |

(52) U.S. Cl.
CPC ............... *C08G 77/26* (2013.01); *A61K 8/898* (2013.01); *A61Q 5/02* (2013.01); *A61Q 5/06* (2013.01); *A61Q 5/12* (2013.01); *C08G 77/06* (2013.01); *C08L 83/10* (2013.01); *C09D 183/08* (2013.01); *C11D 3/001* (2013.01); *C11D 3/3742* (2013.01); *C11D 11/0017* (2013.01); *D06M 13/46* (2013.01); *D06M 15/643* (2013.01); *D06M 15/6433* (2013.01); *D06M 15/651* (2013.01); *A61Q 19/00* (2013.01); *C08G 77/14* (2013.01); *C08G 77/388* (2013.01)

(58) Field of Classification Search
None
See application file for complete search history.

(56) References Cited

U.S. PATENT DOCUMENTS

| | | | |
|---|---|---|---|
| 4,833,225 A | 5/1989 | Schaefer et al. | |
| 7,964,694 B2 | 6/2011 | Ferenz et al. | |
| 2004/0048996 A1 | 3/2004 | Lange et al. | |
| 2004/0138400 A1 | 7/2004 | Lange et al. | |
| 2006/0163524 A1* | 7/2006 | Lange | A61K 8/416 252/8.63 |
| 2007/0106045 A1 | 5/2007 | Lange et al. | |
| 2009/0142293 A1 | 6/2009 | Wagner et al. | |
| 2011/0037012 A1 | 2/2011 | Ferenz et al. | |
| 2015/0037273 A1 | 2/2015 | Wagner et al. | |
| 2015/0299400 A1 | 10/2015 | Wagner et al. | |

FOREIGN PATENT DOCUMENTS

| | | |
|---|---|---|
| WO | 2004/046452 A2 | 6/2004 |
| WO | 2004/090007 A2 | 10/2004 |
| WO | 2009/115412 A1 | 9/2009 |

OTHER PUBLICATIONS

International Search Report and Written Opinion mailed Jun. 21, 2013.

* cited by examiner

*Primary Examiner* — Susan Tran
(74) *Attorney, Agent, or Firm* — Joseph S. Ostroff

(57) ABSTRACT

Low viscosity polyorganosiloxanes comprising a) at least one polyorganosiloxane group, b) at least one quaternary ammonium group, c) at least one terminal group, selected from the groups consisting of: c1) at least one terminal mono functional polyorganosiloxane group, c2) at least one terminal ester group, and c3) at least one terminal alkyl-terminated poly ether group, compositions thereof, aqueous emulsions thereof, methods of the manufacture thereof and their use for the modification of surfaces of substrates.

19 Claims, No Drawings

LOW VISCOSITY POLYORGANOSILOXANES COMPRISING QUATERNARY AMMONIUM GROUPS, METHODS FOR THE PRODUCTION AND THE USE THEREOF (II)

CROSS-REFERENCE TO RELATED APPLICATIONS

This application claims priority to U.S. Provisional Patent application Ser. No. 61/617,180 filed Mar. 29, 2012.

FIELD OF THE INVENTION

The present invention provides for a polyorganosiloxane having a low viscosity and comprising quaternary ammonium groups and terminal ester groups, methods for the production and use thereof.

BACKGROUND OF THE INVENTION

Silicone quats (silicones containing quaternary ammonium groups optionally containing polyorganosiloxane substituents) are known to be highly substantive. DE 3719086 describes the reaction of α,ω-diepoxides with tertiary amines in the presence of acids yielding α,ω-diquaternary siloxanes. They can be used for hair care purposes. DE 3719086 describes tetra alkyl derivatives as well as aromatic imidazolinium derivatives.

The reaction of α,ω-diepoxides with di-tertiary amines in the presence of acids yields polyloop polyquaternary polyorganosiloxanes (EP-A-282720). The advantage of these materials is an improved wash off resistance from hair.

The reaction of α,ω-diepoxides with dimethylamine in the presence of acids yields polyloop polyquaternary polyorganosiloxanes having one quat group between the siloxane blocks is disclosed in U.S. Pat. No. 6,730,766.

Polyquaternary imidazolinium derivates are described in U.S. Pat. No. 6,240,929. These cationic compounds possess an improved compatibility with anionic surfactants in cosmetic formulations.

The incorporation of alkylene oxide moieties in silicone quats is to further increase the hydrophilicity.

Silicone quats containing quat groups as well as polyethylene oxide moieties in side chains are described in U.S. Pat. No. 5,098,979, U.S. Pat. No. 5,153,294 and U.S. Pat. No. 5,166,297. The substantivity of the materials is relatively low.

Silicone based block copolymers containing quat functions that also include polyether moieties are described in WO 02/10257, WO 02/10259 and US 2002/0103094 A. The alkylene oxide structures are incorporated into the block copolymer as α,ω-difunctional moieties.

U.S. Pat. No. 6,242,554 describes α,ω-difunctional siloxane derivatives containing one polyether and one quat function separated from each other. The substantivity of these monoquats is insufficient.

U.S. Pat. No. 4,921,895 describes blends of polyethersiloxanes and quaternary ammonium groups containing siloxane block copolymers for textile finishing purposes. Here, the usage of the polyethersiloxane improves the finished goods and hydrophilicity.

US 2007/0286837, US 2007/0041929, US 2008/0292575 and CN 101198311 describe combinations between silicone quats having a siloxane chain length of greater than 200 D-units and a second silicone for hair conditioning purposes. One possible choice of the second silicone is the choice of silicone polyethers derived from ethylene oxide or propylene oxide or mixtures thereof. Specific structures are not given.

None of the above prior art disclosures describes a straight forward methodology for the preparation of low viscosity polyorganosiloxanes comprising quaternary ammonium groups.

SUMMARY OF THE INVENTION

The present invention provides for a low viscosity silicone (oligomerimeric or polymeric siloxane that is a homopolymer, copolymer or terpolymer) functionalized with quaternary ammonium groups and comprising one or more terminal ester groups as follows: a polyorganosiloxane compound comprising:
  a) at least one polyorganosiloxane group,
  b) at least one quaternary ammonium group,
  c) at least one terminal group, selected from the groups consisting of:
    c1) at least one terminal monofunctional polyorganosiloxane group,
    c2) at least one terminal ester group, and
    c3) at least one terminal alkyl-terminated polyether group.

In a preferred embodiment the polyorganosiloxane compound according to the invention comprises at least one terminal ester group c2).

In a still preferred embodiment the polyorganosiloxane compound according to the invention have e molar ratio of the quaternary ammonium groups b) and the terminal ester groups c2) is less than 100:15, more preferred less than 100:20.

in a further preferred embodiment of the invention the polyorganosiloxane compound does not contain polyalkylene oxide groups except for the terminal group, that is, the the terminal groups may comprise polyalkylene oxide groups, such as the terminal alkyl-terminated polyether group c3), but the polymer main chain does not contain internal polyalkylene oxide groups.

In a further preferred embodiment the polyorganosiloxane compound according to the invention further comprises at least one functional group selected from:
  d) reactive groups,
  e) branching groups, including branched charged groups,
  f) polyalkylene oxide groups, selected from polyalkylene oxide groups lateral to the polymer main chain, and polyalkylene oxide groups axial in the polymer main chain. (These polyalkylene oxide groups are no terminal groups).

The present invention further provides for a method of preparing the compounds of the present invention comprising the reaction of
  (i) at least one ditertiary diamine and/or secondary monoamine,
  (ii) at least one amino-alkylating compound, comprising at least one diepoxide,
  (iii) at least one monofunctional compound selected from monofunctional organic acids, amino-alkylating monofunctional polyorganosiloxane compounds and monofunctional alkyl-terminated polyether compound, selected from amino-functional alkyl-terminated polyether compounds and amino-alkylating alkyl-terminated polyether compound, and
  (iv) optionally a functional precursor compound comprising reactive groups, branching groups, including branched charged groups, polyalkylene oxide groups, selected from polyalkylene oxide groups lateral to the polymer main chain, and polyalkylene oxide groups axial in the polymer main chain, wherein at least one compound among compounds (i) and (ii) comprises polyorganosiloxane structural units.

DETAILED DESCRIPTION OF THE INVENTION

The present invention provides for low viscosity polyorganosiloxanes comprising quaternary ammonium groups, their manufacture and the use of the materials.

Surprisingly, polyorganosiloxanes comprising quaternary ammonium groups possessing a low viscosity is accomplished by the preparation of polyorganosiloxane compounds comprising quaternary ammonium groups and certain terminal groups, preferably terminal ester groups. That is, in accordance with the present invention polyorganosiloxane compounds are provided comprising:

a) polyorganosiloxane groups,
b) quaternary ammonium groups,
c) terminal groups selected from the groups consisting of:
c1) at least one terminal monofunctional polyorganosiloxane group,
c2) at least one terminal ester group, and
c3) at least one terminal alkyl-terminated polyether group.

In a preferred embodiment the terminal group is an ester group c2) and the molar ratio of the quaternary ammonium groups b) and the terminal ester groups c) is less is less than 100:15, preferably less than 100:20.

The polyorganosiloxane compounds according to the invention preferably are linear copolymer compounds that comprise the above functional groups a), b), and the terminal groups being selected from c1) to c3). A preferred terminal group is a terminal ester group that results in particular from the use of monofunctional organic acids as chain stoppers. Formally the resulting copolymers are [C-(A-B)$_x$-A-C]- or [C—(B-A)$_x$-B—C]-type products (wherein x>1, preferably ≥2). The terminal groups C result from the use of monofunctional chain terminating compounds, providing for the groups c1) to c3), whereas A and B usually result from polyfunctional, in particular, difunctional chain-forming monomers. These chain-forming monomers provide the polyorganosiloxane groups a) and the quaternary ammonium groups b). Depending on the molar ratios of the monomers corresponding to A, B and C it may be that part of the terminal groups are formed by the polyfunctional monomers A or B, e.g. [(A-B)$_x$-A]-type products, or [(B-A)$_x$-B]-type products.

However, depending on the stoichiometry of the reactants the polyorganosiloxane compounds according to the invention may also comprise compounds resulting from the reaction of a difunctional monomer with just one compound at each terminal thereof ([(A-B)$_x$-A]-type product (where x=1).

In a preferred embodiment the polyalkylene oxide group f) is an axial group in the polymer main chain and has the general formula:

-A-E-A'- wherein A and A' each are independently from each other selected from a single bond or a divalent organic group having up to 10 carbon atoms and optionally having one or more hetero atoms, and
E is a polyalkylene oxide group of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s=1 to 600.

In a preferred embodiment the groups A and A' are selected from groups that result from the reaction of difunctional alkylating polyalkylene oxide compounds with di-tertiary amines (leading to quaternary ammonium groups) or with di-primary or secondary amines (leading to amine or ammonium groups). Such linking groups A and A' may include for example:
a single bond,
—CH$_2$CH(CH$_3$)—
—[CH$_2$CH$_2$O]$_q$—[CH$_2$CH(CH$_3$)O]$_r$—[CH$_2$CH(C$_2$H$_5$)O]$_s$—
—CH$_2$C(O)O—, —CH$_2$CH$_2$C(O)O—, —CH$_2$CH$_2$CH$_2$C(O)O—, —OC(O)CH$_2$—, —OC(O)CH$_2$CH$_2$—, —OC(O)CH$_2$CH$_2$CH$_2$—, —CH$_2$C(O)—, —CH$_2$CH$_2$C(O)—, —CH$_2$CH$_2$CH$_2$C(O)—, —C(O)CH$_2$—, —C(O)CH$_2$CH$_2$—, —C(O)CH$_2$CH$_2$CH$_2$—,
—CH$_2$CH(OH)CH$_2$—, —O—CH$_2$CH(OH)CH$_2$—, —CH$_2$CH(OH)CH$_2$—O—,
—[CH$_2$CH$_2$O]$_q$—[CH$_2$CH(CH$_3$)O]$_r$—[CH$_2$CH(C$_2$H$_5$)O]$_s$—

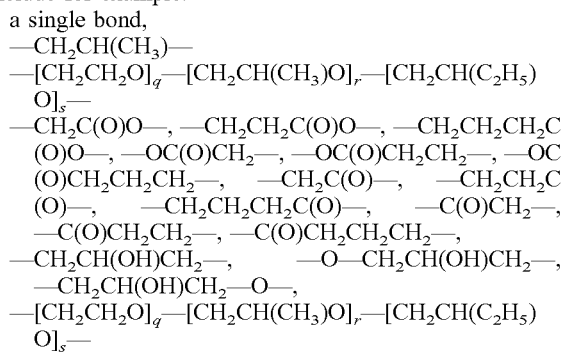

In a preferred embodiment the polyorganosiloxane compounds of the invention do not contain polyalkylene oxide groups except for polyalkylene oxide groups in the terminal ester groups, like in particular those of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s=1 to 600.

In a preferred embodiment of the polyorganosiloxane compounds according to the invention the at least one polyorganosiloxane groups are of the general formula:

—K—S$^1$—K—, with

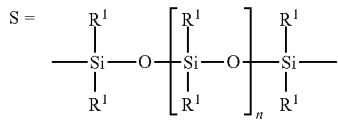

wherein R$^1$=C$_1$-C$_{22}$-alkyl, C$_1$-C$_{22}$-fluoralkyl or aryl,
n=0 to 1000, preferred 0 to 500, more preferred 0 to 300, even more preferred 0 to 200, specifically 0 to 100 or in some instances >200 to 1000, and these can be identical or different if several $S^1$ groups are present in the polyorganosiloxane compound, preferably for example n is for example in the range 0-200 or >200 to 1000;

K=is a bivalent or trivalent straight chain, cyclic and/or branched $C_2$-$C_{40}$ hydrocarbon residue which is optionally interrupted by —O—, —NH—, trivalent N, —NR$^1$—, —C(O)—, —C(S)—, and optionally substituted with —OH, wherein $R^1$ is defined as above, whereby the residues K can be identical or different from each other. In such group —K—S—K— the residue K is bound to the silicon atom of the residue S via a C—Si-bond.

Furthermore, $R^1$ is preferably $C_1$-$C_{18}$ alkyl, $C_1$-$C_{22}$ fluoroalkyl, such as $C_mF_{2m+1}CH_2CH_2$— wherein m has a value of from 1 to 20, and aryl. Furthermore, $R^1$ is preferably $C_1$-$C_6$ alkyl, fluoro-($C_1$-$C_6$)-alkyl-ethyl, more preferably fluoro($C_1$-$C_4$)-alkyl-ethyl, and phenyl. Even more preferably, $R^1$ is methyl, ethyl, 3,3,3-trifluoropropyl, 2-phenylethyl, phenylpropyl or phenyl.

In the framework of the present invention, the term "$C_1$-$C_{22}$ alkyl" means preferably that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "$C_1$-$C_{22}$ fluoroalkyl" preferably means aliphatic hydrocarbon compounds with 1 to 22 carbon atoms which can be straight chain or branched and are substituted with at least one fluorine atom, such as, for example, $CFH_2CH_2CH_2$—, $CF_3CH_2CH_2$—, $C_4F_9CH_2CH_2$—, $C_6F_{13}CH_2CH_2$—, or fluoroalkylethers such as $C_2F_5$—$O(CF_2$—$CF_2$—$O)_{1-9}$-alkyl, $CF_2$—, $F[CF(CF_3)$—$CF_2$—$O]_{1-5}$—$(CF_2)_{0-2}$-alkyl, $C_3F_7$—$OCF(CF_3)$-alkyl and $C_3F_7$—$OCF(CF_3)$—$CF_2$—$OCF(CF_3)$-alkyl, In the framework of the present invention, the term "aryl" means preferably aryl radicals, an unsubstituted or substituted phenyl group once or several times with OH, F, Cl, $CF_3$, $C_1$-$C_6$alkyl, $C_1$-$C_6$-alkoxy, $C_3$-$C_7$-cycloalkyl, $C_2$-$C_6$-alkenyl or phenyl such tolyl, xylyl. "Aryl" means also aralkyl radicals, such as benzyl, 2-phenylethyl or phenylpropyl. The expression can also mean naphthyl if need be.

In a preferred embodiment the polyorganosiloxane compounds according to the invention comprise at least one repeating unit comprising at least one quaternary ammonium group selected from the general formulas:

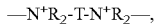

a saturated or unsaturated mono or diquaternary heterocycle of the formulae

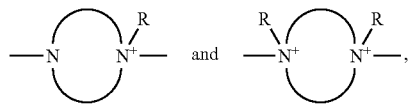

and
an aromatic ammonium heterocycle of the formula

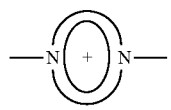

wherein R is selected from monovalent organic groups having up to 22 carbon atoms and optionally one or more heteroatoms, and wherein the free valencies at the nitrogen atoms are bound to carbon atoms. In a preferred embodiment in the group —($N^+R_2$-T-$N^+R_2$)— the groups R preferably represent a monovalent straight chain, cyclic or branched $C_1$-$C_{20}$ hydrocarbon radical, which can be interrupted by one or more —O—, —C(O)— and can be substituted by —OH.

T is selected from a divalent organic group having up to 20 carbon atoms, preferred 2 to 10 carbon atoms, and one or more hetero atoms, in particular, oxygen and nitrogen atoms. In the present invention the term quaternary ammonium group relates to a positively charged nitrogen atom that binds to 4 carbon atoms (formally known as $NR_4^+$ groups).

T preferably represents a divalent straight-chain, cyclic, or branched $C_1$-$C_{20}$, preferred $C_2$-$C_{10}$ hydrocarbon radical, which can be interrupted by —O—, —C(O)— and can be substituted by hydroxy.

Due to the possible presence of amine groups in the polyorganosiloxane compounds according to the invention, they may have protonated ammonium groups, resulting from the protonation of such amine groups with organic or inorganic acids. Such compounds are sometimes referred to as acid addition salts of the polyorganosiloxane compounds according to the invention.

In the polyorganosiloxanes of the invention the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be inter alia modified based upon the selection of acids used.

The terminal monofunctional polyorganosiloxane groups c1) is different from the polyorganosiloxane group a), in that the monofunctional polyorganosiloxane groups c1) have a terminal non-functionalized triorganosilyl group, in particular a trialkylsilyl group, preferably a trimethysilyl group. Such monofunctional polyorganosiloxane groups c1) result from monofunctional, in particular, alkylating polyorganosiloxane compounds, in particular, polydimethylsiloxanes having one terminal functional, in particular, alkylating group, like in particular monoepoxy-functional siloxane compounds. In contrast the polyorganosiloxane groups a) are internal polyorganosiloxane groups in the polymer main chain, that result from multifunctional, in particular difunctional polyorganosiloxanes, in particular, having more than one functional, in particular alkylating groups, like in particular diepoxy polyorganosiloxanes.

In a preferred embodiment of the polyorganosiloxane compounds according to the invention the at least one terminal monofunctional polyorganosiloxane groups c1) is of the general formula:

with $S^2$ is selected from the formulas:

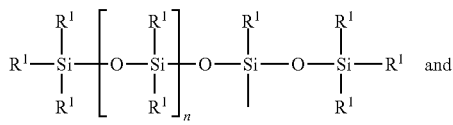

-continued

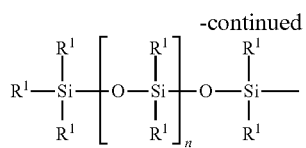

wherein $R^1$ and n are as defined above, preferably
$R^1=C_1-C_{22}$-alkyl, fluor $(C_1-C_{18})$-alkyl-ethyl, $C_6-C_{10}$ aryl, 2-phenylethyl or 2-phenylpropyl,
n1=0 to 1000,
and these can be identical or different if several $S^2$ groups are present in the polyorganosiloxane compound. Preferably n1 is in the range 0-200 or >200 to 1000.

K (in the group —K—$S^2$) is preferably a bivalent or trivalent straight chain, cyclical or branched $C_2-C_{20}$ hydrocarbon residue which is optionally interrupted by —O—, —NH—, trivalent N, —$NR^1$—, —C(O)—, —C(S)—, and optionally substituted with —OH.

$R^1$ is more preferred $C_1-C_{18}$ alkyl, fluoro $(C_1-C_{18})$-alkyl-ethyl or a fluoroalkyl ether and aryl. Furthermore, $R^1$ is preferably $C_1-C_{18}$ alkyl, fluoro$(C_1-C_6)$-alkyl-ethyl, aryl, 2-phenylethyl or phenylpropyl. Furthermore, $R^1$ is preferably $C_1-C_6$ alkyl, fluoro$(C_1-C_6)$-alkyl-ethyl, more preferably fluoro$(C_1-C_4)$-alkyl-ethyl, phenyl, 2-phenylethyl or phenylpropyl. Even more preferably, $R^1$ is methyl, ethyl, trifluoropropyl and phenyl, 2-phenylethyl or phenylpropyl, most preferably $R^1$ is methyl.

In a preferred embodiment of the invention the terminal ester groups are selected from the group of:
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms, optionally comprising one or more hetero atoms. In the case of more than one Z in a terminal ester group identical or different Z structures can be used.

As will be explained in detail below these terminal ester groups result from the use of monofunctional organic acids, like carboxylic acids, e.g. carboxylic acids having from 6 to 30 carbon atoms, preferably 8 to 22 carbon atoms, preferably dodecanoic acid, lauric acid, stearic acid, oleic acid, myristic acid, and alkylpolyether carboxylic acids (—OC(O)—Z), sulfonic acids, like alkyl sulfonic acids, aryl sulfonic acids and alkylarylsulphonic acids (—OS(O)$_2$—Z), sulfuric acid half esters (—OS(O$_2$)O—Z), phosphoric acid mono esters like phosphoric acid alkyl/aryl mono esters (—OP(O)(O—Z)OH), phosphoric acid diesters, like phosphoric acid alkyl/aryl diesters (—OP(O)(O—Z)$_2$) in the reaction with diepoxides.

In a preferred embodiment Z in
—OC(O)—Z
—OS(O)$_2$—Z
—OS(O$_2$)O—Z
—OP(O)(O—Z)OH
—OP(O)(O—Z)$_2$
is a straight chain, cyclic or branched saturated or unsaturated $C_1-C_{20}$, preferred $C_2$ to $C_{18}$, even more preferred $C_{10}$ to $C_{18}$ hydrocarbon radical, which can be interrupted by one or more —O—, or —C(O)— and can be substituted with —OH.

Preferred Z in —OC(O)—Z is resulting from carboxylic acids in particular with more than 10 carbon atoms like for example dodecanoic acid, octadecanoic acid, oleic acid, rhicinolic acid, and undecenic acid.

In a preferred embodiment the polyorganosiloxane compounds according to the invention comprise terminal alkyl-terminated ether and polyether groups c3), which are selected from the general formula:

-A-E-$R^4$ wherein A is as defined above, and $R^4$ is an alkyl group with up to 10 carbon atoms, optionally containing heteroatons, for example oxygen, and hydroxyl groups
with
E a polyalkylene oxide group of the general formulae:

—[CH$_2$CH$_2$O]$_q$—[CH$_2$CH(CH$_3$)O]$_r$—[CH$_2$CH(C$_2$H$_5$)O]$_s$— with
q=0 to 200,
r=0 to 200,
s=0 to 200
and q+r+s=0 to 600.

Achtuung: hier sollte das Folgende berficksichtigt werden:
Der Polyetheranteil muss auf Summe q+r+s=0 gesetzt werden konnen, da z.B monofunktionelle Epoxide, wie z.B. Isopropylglycidether auch funktionieren könnten. Diese Kohlenwasserstoffmonoepoxide sollten wir formal abdecken.

In a further preferred embodiment of the invention the reactive groups d) are selected from groups that can be activated thermally and/or catalytically and/or by the addition of water and/or pH changes.

In a further preferred embodiment of the invention the reactive groups d) are selected from groups of the formulae (I) and (II):

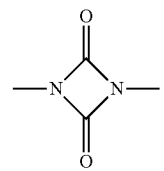

and

—Si(OR)$_{3-a}$(R)$_a$     (II)

in which a is an integer from 0 to 2 and R is as defined above. The introduction of such reactive groups into the polyorganosiloxane copolymers according to the invention is described in detail in particular in WO2004/090007, which is included here completely by reference.

In a further preferred embodiment the polyorganosiloxane compounds according to the invention have branching groups e) of the formula:

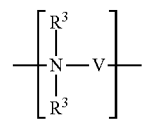

in which $R^3$ are in each case independently organic groups which each contain at least one group which is selected from quaternary ammonium groups and amine oxide groups,
V is selected from the $V^1$ and the $V^2$ group,
in which
$V^2$ is selected from divalent and trivalent, straight-chain, cyclic and branched, saturated, unsaturated and aromatic hydrocarbons having up to 1000 carbon atoms (not counting the carbon atoms of the polysiloxane radical $Z^2$ defined below), which may optionally contain one or more groups selected from
—O—,
—NR$^2$—,
—N$^+$R$^2{}_2$—.
in which R$^2$ is hydrogen, a monovalent, straight-chain, cyclic or branched, saturated, unsaturated or aromatic hydrocarbon radical which has up to 100 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —NR$^2$— groups is present, they may be the same or different,
—C(O)—,
—C(S)—
and
the V$^2$ radical may optionally be substituted by one or more hydroxyl groups, and
the V$^2$ radical contains at least one —Z$^2$— group of the formula

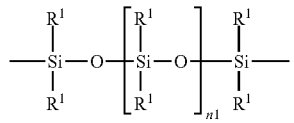

in which
R$^1$ may be the same or different and is selected from the group consisting of: C$_1$ to C$_{22}$ alkyl, fluoro(C$_1$-C$_8$) alkylethyl- and C$_6$-C$_{10}$ aryl, 2-phenylethyl and phenylpropyl, and
n$_1$=20 to 1000,
V$^1$ is selected from divalent and trivalent, straight-chain, cyclic and branched, saturated, unsaturated and aromatic hydrocarbon radicals which have up to 1000 carbon atoms and may optionally contain one or more groups selected from
—O—,
—NR$^2$—,
—N$^+$R$^2{}_2$—.
in which R$^2$ is as defined above, and where the R$^2$ groups in the V$^1$ and V$^2$ groups may be the same or different,
—C(O)—,
—C(S)— and
—Z$^1$—, in which —Z$^1$— is a group of the formula

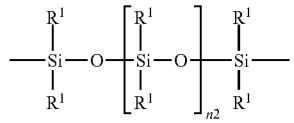

in which
R$^1$ is as defined above, where the R$^1$ groups in the V$^1$ and V$^2$ groups may the same or different, and
n$_2$=0 to 19,
and the V$^1$ radical may optionally be substituted by one or more hydroxyl groups, in which the V$^1$ and V$^2$ groups in the polyammonium/polysiloxane copolymers may be the same or different, with the proviso that at least one Z$^1$ or Z$^2$ group is present, and in which the positive charges resulting from the ammonium groups are neutralized by organic or inorganic acid anions. The introduction of such branching groups into polyorganosiloxane compounds is described in particular in detail in WO2007/014930.

In a preferred embodiment R$^3$ is a group of the formula:

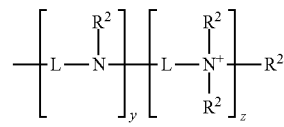

in which
L are in each case independently a divalent straight-chain, cyclic or branched, saturated, unsaturated or aromatic hydrocarbon radical which has up to 30 carbon atoms and may contain one or more groups selected from —O—, —NH—, —C(O)— and —C(S)—, and which may optionally be substituted by one or more substituents selected from the group consisting of a hydroxyl group, a carboxyl group, a carboxylate group, an optionally substituted heterocyclic group preferably containing one or more nitrogen atoms, amino, alkylamino, dialkylamino, ammonium group, polyether radicals and polyetherester radicals,
the groups R$^2$ are the same or different and each are as defined above, and
z is 1 to 10 and y may be 0 to 10.

In a further preferred embodiment R$^3$ is a group of the formula:

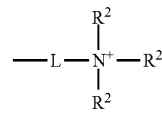

wherein L and R$^2$ are each as defined above, and the groups R$^2$ may be the same or different groups.

In a further preferred embodiment R$^3$ is a group of the formula:

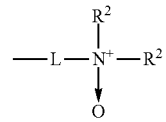

wherein L and R$^2$ are each as defined above, and the groups R$^2$ may be the same or different groups.

In a further preferred embodiment the branching group e) is a
trivalent or higher valent organopolysiloxane group S$^v$ which has at least three silicon atoms. S$^v$ includes equilibration and condensation products. These polyorganosiloxanes comprise siloxane units M, D, T, and Q (W. Noll, Chemie und Technologie der Silicone, [=Chemistry and Technology of Silicones], VCH, Weinheim, 1968) as well as units M', D', and T' which are derived from M-, D-, and T-units in which formally by omission of a methyl group a free valence is formed.

Examples of the $S^v$ groups include, for example, at least trivalent organopolysiloxane groups of the structures $S^{vI}$ and $S^{vII}$:

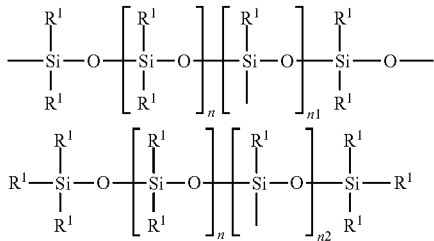

with n1≥1 ($S^{vI}$) and n2≥3 ($S^{vII}$)

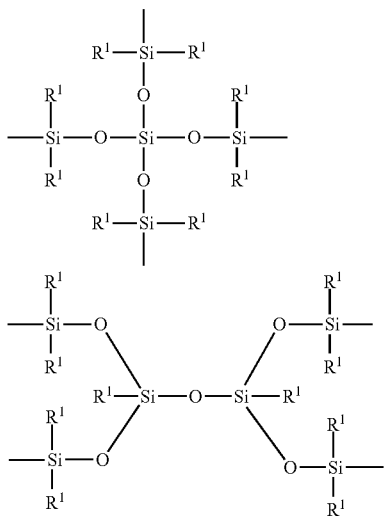

In an additionally preferred embodiment of the invention the branching group e) is represented by the formula $V^{1v}$ where $V^{1v}$ is a trivalent or higher valent group which is connected to amino or quaternized nitrogen atoms.

$V^{1v}$, which is connected to the amino or quaternized nitrogen atoms, comprises moieties selected from the group of consisting of

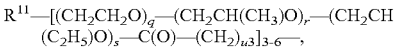

which are bound to a trivalent to hexavalent group which is derived from a polyol in which 3 to 6 hydroxyl-hydrogen atoms are substituted, q=0 to 200, preferred 0 to 100, more preferred 0 to 50, still more preferred 0 to 20, r=0 to 200, preferred 0 to 100, more preferred 0 to 50, still more preferred 0 to 20, s=0 to 200, preferred 0 to 100, more preferred 0 to 50, still more preferred 0 to 20, and q+r+s=1 to 600, preferred 1 to 100, more preferred 1 to 50, even more preferred 1 to 40, u3=1 to 3, or

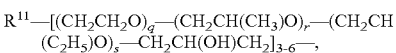

which are bound to a trivalent to hexavalent group which is derived from a polyol in which 3 to 6 hydroxyl-hydrogen atoms are substituted, q, r, s are defined as above.

It is within the scope of the invention to incorporate other polyether structures into $R^{11}$. Examples are polyether structures derived from 1,3-propane diol, 1,2-butane diol, 1,4-butane diol.

The aforementioned polyol is preferably chosen from the group which consists of: glycerol, trimethylolpropane, pentaerythritol, sorbitol, and sorbitan. Examples for $V^{1v}$ also include: trivalent and higher valent structures based on esters of glycols and polyglycols with $C_2$ to $C_{10}$-polycarboxylic acids or ethers of beta-hydroxyalkyl groups, proceeding from the conversion of polyols with oxirans, such as epichlorohydrine, vinylcyclohexene monoepoxide, vinylcyclohexene diepoxide.

Preferred polyols are glycerol, trimethylolpropane, pentaerythritol, sorbitol, and sorbitan, which can also be directly esterified with chloroacetic acid or chloropropionic acid.

Examples for this type of branching group e) with q=v and r=w are

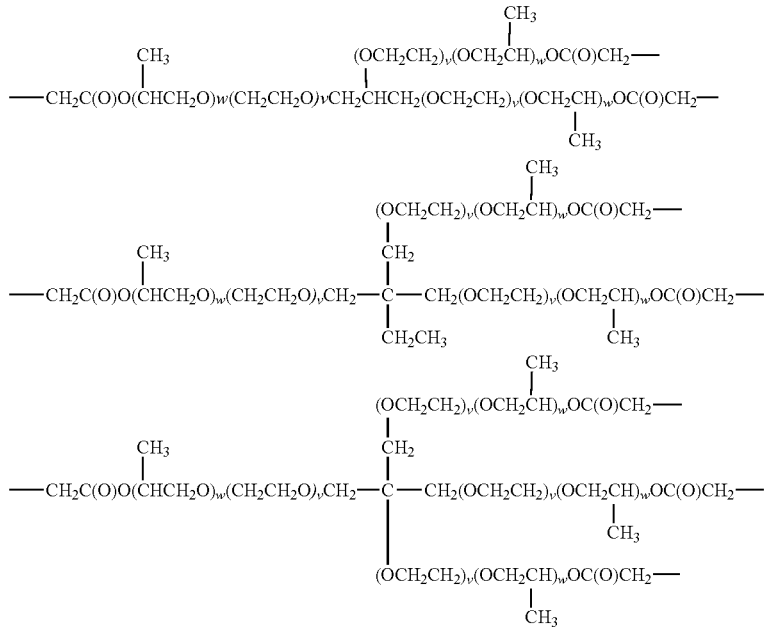

-continued

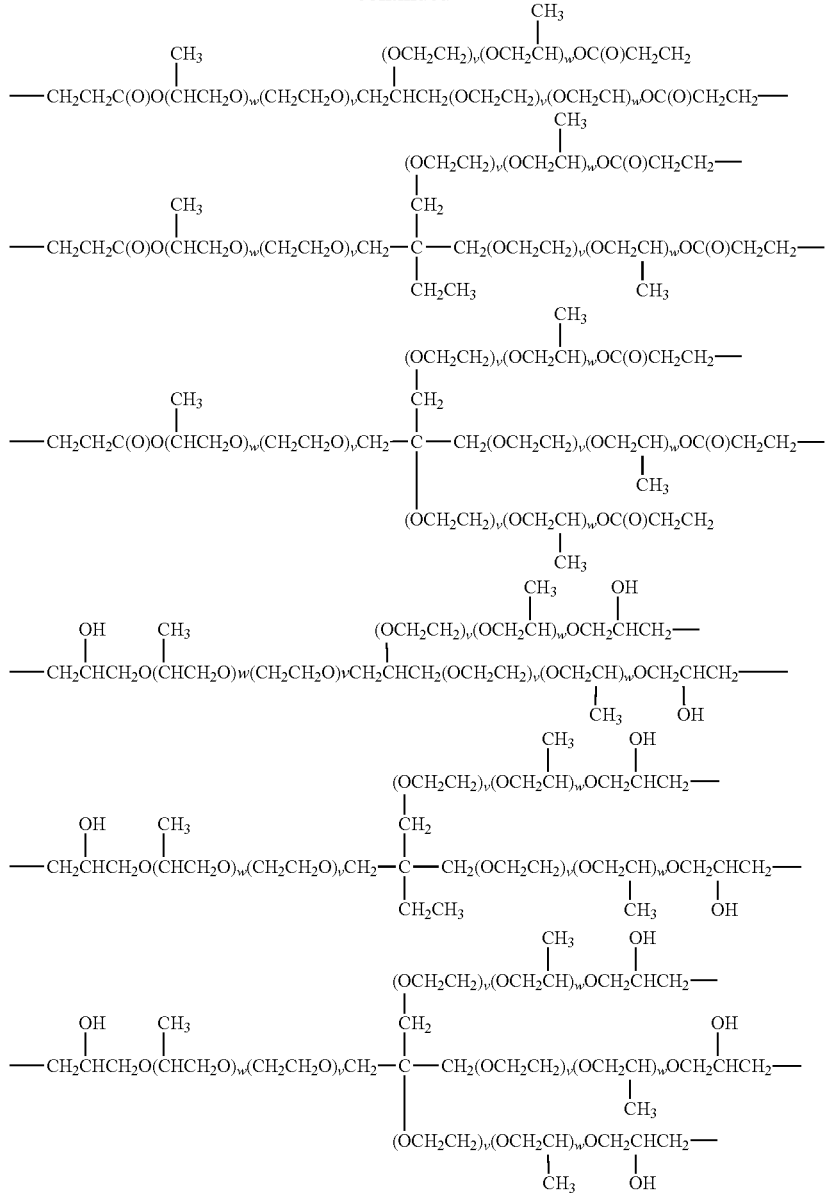

with v+w=q+r≥0.

Alternatively, $V^{1v}$ is a nitrogen centered group, for example selected from

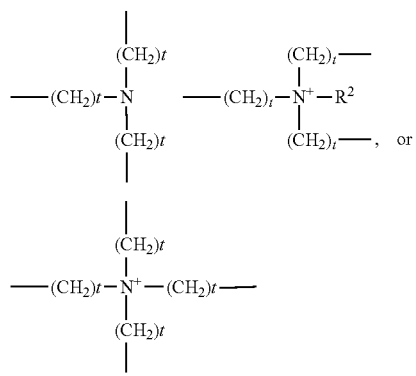

where t is from 2 to 10 and $R^2$ is defined as above, preferably H or methyl.

It is within the scope of the invention to replace —$(CH_2)_t$— fully or partially by the above described polyether moieties. Examples for compounds which can yield these nitrogen centred $V^{1v}$ are triethanolamine and it's ethoxylates, $N[CH_2CH_2N(CH_3)_2]_3$, $N[CH_2CH_2CH_2N(CH_3)_2]_3$ and N,N,N',N'',N''-pentamethyl dipropylene triamine.

In an additional preferred form of embodiment of the invention the branching group g) is represented by the formula $$V^{2v}$$

which is connected to a siloxane chain via an —Si—C— bond and where $V^{2v}$ is a trivalent or higher valent group which is chosen from the group which consists of:

—$(Z—)_y R^{12}$—$[—(CH_2CH_2O)_q$—$(CH_2CH(CH_3)O)_r$— $(CH_2CH(C_2H_5)O)_s$—CO—$(CH_2)_{u3}]_z$—, where $R^{12}$ is a trivalent or hexavalent group which is derived from a polyol in which 3 to 6 hydroxyl-hydrogen atoms are substituted, and Z in this context is a divalent hydrocarbon group with up to 20 carbon atoms which can contain one or more groups chosen from —O— and —C(O)—, and which, in given cases, can be substituted with one or more hydroxyl groups, and where the group Z is bonded by one of its carbon atoms to a silicon atom, q=0 to 200, preferred 0 to 100, more preferred 0 to 50, still more preferred 0 to 20, r=0 to 200, preferred 0 to 100, more preferred 0 to 50, still more preferred 0 to 20, s=0 to 200, preferred 0 to 100, more preferred 0 to 50, still more preferred 0 to 20, and q+r+s=1 to 600, preferred 1 to 100, more preferred 1 to 50, even more preferred 1 to 40, u3=1 to 3, y=1 to 6, preferably 1, z=0 to 5, preferably 2 to 5, and z+y=3 to 6, preferably 3,

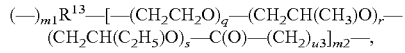

where $R^{13}$ is a trivalent or hexavalent, saturated or unsaturated, linear, branched or cyclic hydrocarbon group with up to 10 carbon atoms, (—) represents a single bond to a silicon atom, q=0 to 200, preferred 0 to 100, more preferred 0 to 50, still more preferred 0 to 20, r=0 to 200, preferred 0 to 100, more preferred 0 to 50, still more preferred 0 to 20, s=0 to 200, preferred 0 to 100, more preferred 0 to 50, still more preferred 0 to 20, and q+r+s=1 to 600, preferred 1 to 100, more preferred 1 to 50, even more preferred 1 to 40, u3=1 to 3, m1=1 or 2, preferably 1, m2=1 to 5, preferably 2 to 5, and m1+m2=3 to 6, preferably 3,

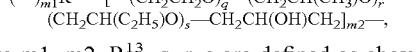

where m1, m2, $R^{13}$, q, r, s are defined as above,

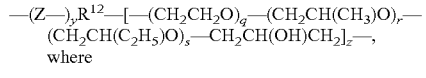

where

Z, y, $R^{12}$, q, r, s and z are defined as above.

Examples of the groups $V^{2v}$ with q=v and r=w include:

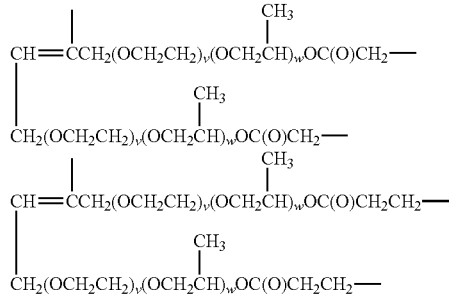

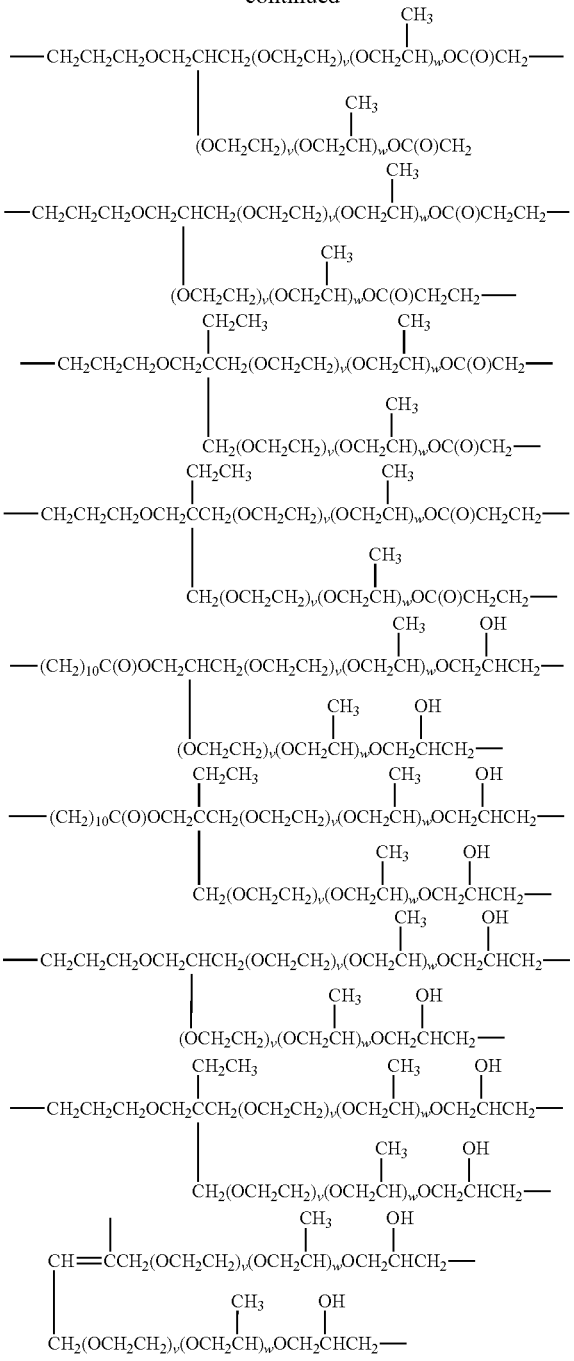

with v+w=q+r≥0.

The molar percentage of $\Sigma S^v + V^{1v} + V^{2v}$ is 0.0001 to 50%, preferably 0.001 to 30%, more preferred 0.01 to 20%, especially 0.1 to 20% based on the molar amount on the corresponding non branching moieties. This means that $S^v$ is compared with non branching siloxane moieties. $V^{1v}$ is compared with non-branching i.e. polyol-polyether moieties or non-branching amino centered moieties. $V^{2v}$ is compared with the non-branching substituents on the silicone atoms.

It is within the scope of the invention to use a single branching concept or more than one of the above described branching concepts based on $S^v$, $V^{1v}$, $V^{2v}$ simultaneously.

Further details of the synthesis and incorporation of the branching groups e) are outlined in U.S. Pat. No. 7,390,479, which is herewith included by reference.

In a preferred embodiment the lateral polyalkylene oxide group f) is a radical $R^o$ of formula (XVIII):

$$—X-E-Y \tag{XVIII}$$

in which X is a single bond or a divalent straight-chain, branched or cyclic hydrocarbon radical which has up to 20 carbon atoms and may optionally contain nitrogen and/or oxygen,
and X is bonded to an amino or quaternized nitrogen atom via a carbon atom,
E is a polyalkylene oxide radical of the formula $$—[(C_aH_{2a})O]_y—$$

in which a=from 2 to 4,
y=from 2 to 10 000,
which is bonded to the X group via a carbon atom and to the Y group via an oxygen atom, Y is hydrogen or a monovalent straight-chain, branched or cyclic, saturated, unsaturated or aromatic hydrocarbon radical which has up to 24 carbon atoms and may contain oxygen and/or nitrogen and/or halogen and is bonded to the E group via a carbon atom. $R^o$ is preferably a group of the formula (XVIII) in which -E- is a group of the formula $$—(OCH_2CH_2)_q—(OCH_2CH(CH_3))_r—(OCH_2CH(C_2H_5))_s—$$

wherein
q preferably 0 to 100, more preferably 0 to 70, even more preferably 0 to 40,
r preferably 0 to 100, more preferably 0 to 70, even more preferably 0 to 40,
s preferably 0 to 100, more preferably 0 to 70, even more preferably 0 to 40,
q+r+s=1 to 300, more preferably 1 to 100, even more preferred 1 to 50.
In the group —(OCH$_2$CH$_2$)$_q$—(OCH$_2$CH(CH$_3$))$_r$—(OCH$_2$CH(C$_2$H$_5$))$_s$— the ethylene oxide and propylene oxide and butylene oxide units can be positioned in any way, e.g. as statistical copolymer units or as a block copolymer unit. It is within the scope of the invention to incorporate other polyether structures into E. Examples are polyether structures derived from 1,3-propane diol and 1,4-butane diol.

In the group of the formula (XVIII), moreover, Y is preferably selected from H and straight-chain, cyclic, branched C1- to C22-alkyl, alkenyl, alkynyl, fluoro(C1-C10)alkyl and C6-C10-aryl radicals.

In a preferred embodiment Y is a straight-chain, cyclic, branched $C_1$- to $C_{12}$-alkyl radical, alkenyl radical, alkynyl radical or C6-C10-aryl radical, especially methyl, ethyl, isopropyl, butyl, hexyl, dodecyl, allyl, oleyl, phenyl.

A further preferred alkylene oxide unit $R^o$ has the structure
—(C1-C12)-alkylene-N$^+$—(R$^2$)$_2$-E-Y
in which C1-C12-alkylene is a straight-chain, cyclic or branched alkylene unit having from 1 to 12 carbon atoms, and $R^2$, E and Y are each as defined above.

This means that the polyether moieties containing lateral or pending chains respectively can contain quaternized moieties.

Further details of the synthesis and incorporation of the pending groups e) are outlined in U.S. Pat. No. 8,076,442, which is herewith included by reference.

In a preferred embodiment the polyorganosiloxane compounds according to the invention have the general formula (I):

$$M—Y—[—(N^+R_2-T-N^+R_2)—Y—]_m M \tag{I')}$$

or $$M—Y—[—(N^+R_2)—Y—]_m-M \tag{II}$$

or $$M—Y—[—(N^+R_2-T-N^+R_2)—Y—]_m—[—(NR^5-A-E-A'-NR^5)—Y—]_k—X_h-M \tag{III}$$

wherein:
m is >0, preferred 0.01 to 100, more preferred 0.1 to 100, even more preferred 1 to 100, specifically 1 to 50, more specifically 1 to 20, even more specifically 1 to 10,
k is 0 or an average value of >0 to 50 preferred 1 to 20, more preferred 1 to 10,
h is 0 to 100, preferred 0.01 to 100, more preferred 0.1 to 100, even more preferred 1 to 100, specifically 1 to 50, more specifically 1 to 20, even more specifically 1 to 10,
R is as defined above,
M represents a terminal group c), selected from the groups consisting of:
c1) at least one terminal monofunctional polyorganosiloxane group,
c2) at least one terminal ester group, and
c3) at least one terminal alkyl-terminated polyether group, preferably a terminal ester groups selected from
—OC(O)—Z
—OS(O)$_2$—Z
—OS(O$_2$)O—Z
—OP(O)(O—Z)OH
—OP(O)(O—Z)$_2$
wherein Z is as defined above,
-A-E-A'- is as defined above,
$R^5$ is selected from hydrogen or R, preferably $R^2$ as defined above,
Y is T, or a group of the formula:
—K—S—K— and -A-E-A'- or -A'-E-A-,
each as defined above, with the proviso that at least one Y is a group of the formula —K—S—K— and
T is a as defined above,
X is least one functional group selected from:
d) reactive groups,
e) branching groups, including branched charged groups, and
f) polyalkylene oxide groups, selected from polyalkylene oxide groups lateral to the polymer main chain, and polyalkylene oxide groups axial in the polymer main chain,
wherein the repeating units having the indices m, k and h, may be arranged in any order, like e.g. randomly, alternately or blockwise.

Preferably the polyorganosiloxane compounds according to invention have a molar ratio of the repeating groups —K—S—K— and the repeating groups -A-E-A'- or -A'-E-A- between 100:1 and 1:100, preferably between 20:1 and 1:20, more preferably between 10:1 and 1:10.

Further preferably the polyorganosiloxane compounds have a molar ratio of the repeating groups —K—S—K— and the group X is between 100:1 and 1:100, preferably between 20:1 and 1:20, even more preferably between 10:1 and 1:10.

In a preferred embodiment of the present invention the polyorganosiloxane compounds have protonated ammonium groups preferably resulting from protonated groups —(N$^+$HR$^5$-A-E-A'-N$^+$HR$^5$)—.

If amine groups are present in the polyorganosiloxane compounds according to the invention, they may be protonated for example with organic or inorganic acids. Such compounds are sometimes referred to as acid addition salts of the polyorganosiloxane compounds according to the invention.

In a preferred embodiment in the polyorganosiloxane compounds the molar ratio of the quaternary ammonium groups b) and the terminal ester groups c) is less than 100:15, preferably less than 100:30 and is most preferred less than 100:50. The ratio can be determined by $^{13}$C-NMR.

In the embodiment where the terminal group is selected from the terminal monofunctional polyorganosiloxane groups c1) or the terminal alkyl-terminated polyether group c3) the molar ratio of the quaternary ammonium groups b) to the terminal monofunctional siloxane groups c1) or the terminal alkyl-terminated polyether group c3) is less than 100:5, more preferred is less than 100:10, even more preferred is less than 100:20 and is most preferred less than 100:30, specifically less than 100:50. The ratio can be adjusted by the stoichiometry of the reactants. These ratios can be determined by $^{13}$C-NMR.

The polyorganosiloxane compounds according to the invention are manufactured preferably by a process, which comprises the reaction of
(i) at least one ditertiary diamine and/or secondary monoamine,
(ii) at least one amino-alkylating compound, comprising at least one diepoxide, and
(iii) at least one monofunctional compound selected from monofunctional organic acids, amino-alkylating monofunctional silicone compounds and monofunctional alkyl-terminated polyether compound, selected from amino-functional alkyl-terminated polyether compounds and amino-alkylating alkyl-terminated polyether compound, and
(iv) optionally a functional precursor compound comprising reactive groups, branching groups, including branched charged groups, polyalkylene oxide groups, selected from polyalkylene oxide groups lateral to the polymer main chain, and polyalkylene oxide groups axial in the polymer main chain,
wherein at least one compound among compounds (i) and (ii) comprises polyorganosiloxane structural units. The molar ratios of the compounds (i) to (iv) are preferably as follows.

In case the at least one monofunctional compound (iii) is selected from amino-alkylating monofunctional silicone compounds and monofunctional alkyl-terminated polyether compound, selected from amino-functional alkyl-terminated polyether compounds and amino-alkylating alkyl-terminated polyether compound, the molar ratio of the component (ii) to (iii) is preferably 90:10 to 50:50.

In a preferred embodiment of the process according to the invention the at least one compound among compounds (i) and (ii) may also comprise the polyalkylene oxide structural units as described before.

The present invention further relates to polyorganosiloxane compounds that are obtainable by the process according to the invention as described before.

A further embodiment of the present invention relates to polyorganosiloxane compositions, comprising:
A) at least one polyorganosiloxane compound, comprising
a) at least one polyorganosiloxane group, and
b) at least one quaternary ammonium group,
c) optionally at least one terminal ester group, and B) at least one polyorganosiloxane compound, which does not have quaternary ammonium groups, and which polyorganosiloxane compound B) comprises at least one terminal ester group.

In the definition of component A) it can be referred to the description of the polyorganosiloxane compounds of the invention. Optionally component A) may comprise
c) at least one terminal group, selected from the groups consisting of:
c1) at least one terminal monofunctional siloxane group,
c2) at least one terminal ester group, and
c3) at least one terminal alkyl-terminated polyether group,
and also may comprise at least one functional group selected from:
d) reactive groups,
e) branching groups, including branched charged groups,
f) polyalkylene oxide groups, selected from polyalkylene oxide groups lateral to the polymer main chain, and polyalkylene oxide groups axial in the polymer main chain.

The polyorganosiloxane compound B) differs from the polyorganosiloxane compound A) in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions according to the invention the weight ratio of compound A) to compound B) is preferably less than 90:10. Or with other words, the content of component B) is at least 10 weight percent. In a further preferred embodiment of the polyorganosiloxane compositions according to the invention in compound A) the molar ratio of the quaternary ammonium groups b) and the terminal ester groups c) is less than 100:20.

The synthesis of the polyorganosiloxane compounds B) is known for example from WO 2011/064255. They can be synthesized i.e. from the corresponding epoxy siloxanes by esterification with acids in the presence of a tertiary amine catalyst. The preferred polyorganosiloxane compounds B) comprising ester functions are α,ω-ester modified derivatives of the structure M-(K—S$^1$—K)-M (with M, K and S$^1$ each as defined above) having siloxane chain length' in a range from n=0 to 1000, preferred 0 to 500, more preferred 0 to 300, even more preferred 0 to 200, specifically 0 to 100. Alternatively, comb-like derivatives comprising ester function as side groups in a difunctional siloxane unit (OSiMeR* with R*=carbon bound ester group), and optionally terminal ester moieties (O$_{1/2}$SiMe$_2$R* with R*=carbon bound ester group) of the same chain length range of n are also preferred. The number of ester-group-containing siloxy units is preferably from 1 to 500, preferred 1 to 250, more preferred 1 to 150, even more preferred 1 to 100, specifically 1 to 50, even more specific 1 to 25. It is within the scope of the invention that ester functions containing polyorganosiloxanes contributing to compound B) are formed during the polymerization reaction by i.e. reaction of the epoxy functionalized siloxanes yielding elements a) and c) with organic acids under ester bond formation. In the latter case mono ester functionalized siloxanes are formed and contribute to compound B).

Preferred monofunctional organic acids yielding the esters are the ones forming the above mentioned counter ions. Preferred examples are C$_1$-C$_{30}$ carboxylic acids, for example C2, C3, C8 acids, C$_{10}$-C$_{18}$ carboxylic acids, for example C12, C14, C16-acids, saturated, unsaturated and hydroxyl functionalized C18-acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Preferably in the polyorganosiloxane composition according to the invention in compound A) the molar ratio of the quaternary ammonium groups b) and the terminal ester groups c) is less than 100:10, preferably less than 100:15, more preferably less than 100:20.

The polyorganosiloxane compounds or polyorganosiloxane compositions according to the invention have a viscosity at 20° C. and a shear rate of 0.1 s$^{-1}$ below 200.000 mPa·s, more preferred below 150.000 mPa·s, more preferred below 100.000 mPa·s, still more preferred 500 to below 100.000 mPa·s, still more preferred 500 to 70.000 mPa·s, still more preferred 500 to 50.000 mPa·s, still more preferred 500 to 20.000 mPa·s, still more preferred 500 to 10.000 mPa·s, and still more preferred 500 to 5.000 mPa·s.

Another embodiment relates to polyorganosiloxanes comprising
A1) at least one polyorganosiloxane compound, comprising
  a) at least one polyorganosiloxane group,
  b) at least one quaternary ammonium group,
  c1) at least one terminal monofunctional siloxane group,
  c2) optionally one or more terminal ester groups, and
  c3) optionally one or more terminal alkyl-terminated polyether groups, and optionally least one functional group selected from:
  d) reactive groups,
  e) branching groups, including branched charged groups,
  f) polyalkylene oxide groups, selected from polyalkylene oxide groups lateral to the polymer main chain, and polyalkylene oxide groups axial in the polymer main chain,
wherein the moieties a), b), c1), c2), c3), d), e) and f) are each as defined above. Such polyorganosiloxanes A1) may be used preferably in compositions with C) at least one non-functionalized polyorganosiloxane compound of the general formula

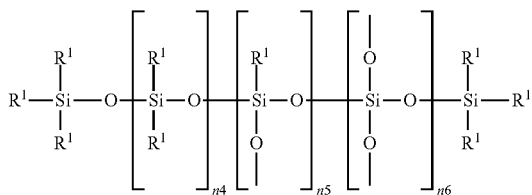

wherein
$R^1$=$C_1$-$C_{22}$-alkyl, $C_1$-$C_{22}$-fluoralkyl, fluoro($C_1$-$C_8$)alkylethyl, aryl, 2-phenylethyl or phenylpropyl,
n4=0 to 2000, preferred 0 to 1000, more preferred 0 to 600, even more preferred 0 to 400, specifically 0 to 200 or in some instances >400 to 2000,
n5=0 to 200, preferred 0 to 20, more preferred 0 to 4, even more preferred 0 to 1, specifically 0 and 1,
n6=0 to 200, preferred 0 to 20, more preferred 0 to 4, even more preferred 0 to 1, specifically 0 and 1,
n4+n5+n6=0 to 2000, preferred 0 to 1000, more preferred 0 to 600, even more preferred 0 to 400, specifically 0 to 200 or in some instances >400 to 2000,
A preferred component C) is in particular a polydimethylsiloxane having an average number of siloxane units of from 10 to 1000, preferably 50 to 500.

In a preferred embodiment polyorganosiloxane compounds C) result i.e. from equilibration reactions targeting high molecular weight monofunctional SiH precursors. Typically, these monofunctional SiH precursors are accompanied by certain quantities of di- and higher functional SiH fluids as well as non functionalized silicone fluids. After a subsequent hydrosilylation step yielding the i.e mono epoxy functionalized silicones these non-functionalized silicones remain in the target product too.

Alternatively, specific grades of separately produced non-functionalized silicone fluids can be added.

In the polyorganosiloxane compositions according to the invention the weight ratio of compound A1) to compound C) preferably ranges from <100:>0 to 50:50, more preferred from <100:>0 to 70:30, even more preferred from 99.5:0.5 to 70:30, specifically from 99:1 to 70:30.

The viscosity of both, the polyorganosiloxane compounds and the polyorganosiloxane compositions according to the invention may depend on the structure and the amount of the least one functional group selected from:
  d) reactive groups,
  e) branching groups, including branched charged groups,
  f) polyalkylene oxide groups, selected from polyalkylene oxide groups lateral to the polymer main chain, and polyalkylene oxide groups axial in the polymer main chain.

However, it is characteristic that the polyorganosiloxane compounds or the polyorganosiloxane compositions according to the invention which contain the terminal monofunctional siloxane groups c1) or the terminal ester groups c2) are lower in viscosity than the corresponding non-inventive compounds or compositions without significant portions of terminal monofunctional siloxane groups c1) or the terminal ester groups c2).

The preferred molecular weight of the polysiloxane compounds A) or A1) according to the invention is between 10.000 and 100.000 g/mol measured as weight average Mw per GPC (gel permeation chromatography) and polystyrene as standard.

The present invention further relates to aqueous emulsions comprising at least one polyorganosiloxane compound and/or at least one polyorganosiloxane composition as defined above or below. Such aqueous emulsions preferably comprise at least 30 weight percent, preferably at least 50 weight percent, still more preferably at least 80 weight percent water based on the total weight of the emulsions.

The present invention further relates to a method of surface treatment, comprising the step of applying the polyorganosiloxane compounds, the polyorganosiloxane compositions or the aqueous emulsions thereof as defined in any of the previous claims, to the surface of a substrate. Any method of applying it is conceivable, e.g. simple wetting, contacting, washing, dipping, spraying, brushing, spreading operations conventionally known in the art can be referred to.

In such method preferably one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

Further Preferred Embodiments of the Invention

In the polyalkylene oxide group E of the general formula:

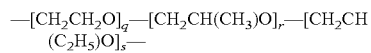

the indices are preferably:
q=0 to 200, preferred 0 to 100, more preferred 0 to 50, still more preferred 0 to 20,
r=0 to 200, preferred 0 to 100, more preferred 0 to 50, still more preferred 0 to 20,
s=0 to 200, preferred 0 to 100, more preferred 0 to 50, still more preferred 0 to 20,
and q+r+s=1 to 600, preferred 1 to 100, more preferred 1 to 50, even more preferred 1 to 40.

In the polyorganosiloxane structural unit with the general formula S:

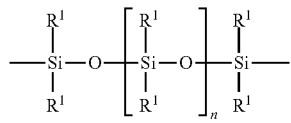

wherein $R^1=C_1$-$C_{22}$-alkyl, $C_1$-$C_{22}$-fluoralkyl or aryl,
n=0 to 1000, preferred 0 to 500, more preferred 0 to 300, even more preferred 0 to 200, specifically 0 to 100 or in some instances >200 to 1000.
K (in the group —K—S—K—) is preferably a bivalent or trivalent straight chain, cyclical or branched $C_2$-$C_{20}$ hydrocarbon residue which is optionally interrupted by —O—, —NH—, trivalent N, —NR$^1$—, —C(O)—, —C(S)—, and optionally substituted with —OH.

In the polyorganosiloxanes of the invention the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be inter alia modified based upon the selection of acids used.

Quaternary ammonium groups as contained in the polyorganosiloxanes of the invention are usually generated by reacting the di-tertiary diamines with an alkylating agents, selected from in particular di-epoxides (sometimes referred to also as bis-epoxides) in the presence of mono carboxylic acids and difunctional dihalogen alkyl compounds.

$R^1$ is more preferred $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ is preferably $C_1$-$C_6$ alkyl, $C_1$-$C_6$ fluoroalkyl, more preferably $C_1$-$C_4$ fluoroalkyl, and phenyl. Even more preferably, $R^1$ is methyl, ethyl, trifluoropropyl and phenyl. Most preferred is methyl for $R^1$.

In the framework of the present invention, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are presented as examples.

In the framework of the present invention, "aryl" means unsubstituted or phenyl substituted once or several times with OH, F, Cl, CF$_3$, $C_1$-$C_6$ alkyl, $C_1$-$C_6$ alkoxy, $C_3$-$C_7$ cycloalkyl, $C_2$-$C_6$ alkenyl or phenyl. The expression can also mean naphthyl if need be.

In a preferred embodiment the polyorganosiloxane compounds are of the general formula (I):

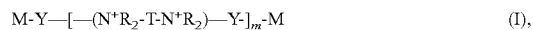

or

or

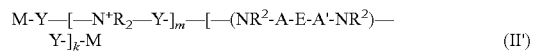

wherein each group is as defined above.
Z in the groups M:
—OC(O)—Z
—OS(O)$_2$—Z
—OS(O$_2$)O—Z
—OP(O)(O—Z)OH
—OP(O)(O—Z)$_2$
is preferably is a straight chain, cyclic or branched saturated or unsaturated $C_1$-$C_{20}$, preferred $C_2$ to $C_{18}$, even more preferred-hydrocarbon radical, which can be interrupted by one or more —O—, or —C(O)— and substituted with —OH.

Preferred groups M are —OC(O)—Z resulting from normal carboxylic acids in particular with more than 10 carbon atoms like for example dodecanoic acid.

In a preferred embodiment of the invention the molar ratio of the polyorganosiloxane-containing repeating group —K—S$^1$—K— and the repeating group Y is between 100:0. As the case may require it may be also 100:1 and 1:100, preferred between 20:1 and 1:20, even more preferred between 10:1 and 1:10.

In a preferred embodiment of the invention the molar ratio of the polyorganosiloxane-containing repeating group —K—S$^1$—K— and the polyalkylene repeating group -A-E-A'- or -A'-E-A- is between 100:1 and 1:100, preferred between 20:1 and 1:20, even more preferred between 10:1 and 1:10.

The molar ratio of the polyorganosiloxane-containing repeating group —K—S$^1$—K— and the polyalkylene repeating group -A-E-A'- or -A'-E-A- can be controlled as shown below via the selection of the molar ratio of the parent compounds, especially the ratio of the α,ω-halogen alkyl carboxylic acid polyalkylene oxide ester compounds preferably used in the invention and the polyorganosiloxane-bis epoxide compounds. The properties of the products depend essentially upon the ratio of the parent materials used, and upon the length of the polyalkylene oxide or polyorganosiloxane blocks contained therein.

In the group —(N$^+$R$_2$-T-N$^+$R$_2$)— the groups R preferably represent a monovalent straight chain, cyclic or branched $C_1$-$C_{20}$ hydrocarbon radical, which can be interrupted by one or more —O—, —C(O)— and can be substituted by —OH, T preferably represent a divalent straight-chain, cyclic, or branched $C_1$-$C_{20}$ hydrocarbon radical, which can be interrupted by —O—, —C(O)— and can be substituted by hydroxyl.

The viscosities of the neat polymers A) or A1) according to this embodiment of the invention preferably are <100000 mPa·s, preferred <70000 mPa·s, more preferred <50000 mPa·s, even more preferred <20000 mPa·s, specifically <10000 mPa·s, more specifically <5.000 mPa·s but preferably does not fall short below 500 mPa·s determined at 20° C. and a shear rate of 0.1 s$^{-1}$.

The molecular weight is between 10,000 and 100,000 g/mol measured as weight average molecular weight Mw per GPC (gel permeation chromatography) and polystyrene as standard.

In a preferred embodiment of the invention, K is a divalent hydrocarbon radical having at least 4 carbon atoms, which contains one hydroxy group and can be interrupted by one oxygen atom. Such groups include for example:

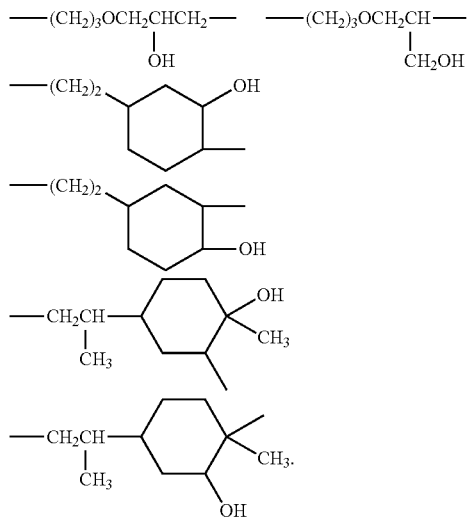

In the group

preferably, the group -A-E-A'- is represented by a group of the formula

-A-(OCH$_2$CH$_2$)$_q$(OCH$_2$CH(CH$_3$))$_r$—(OCH$_2$CH(C$_2$H$_5$))$_s$-A'- wherein A is a single bond or a straight chain or branched C$_1$-C$_6$ alkanediyl group with
q preferably 0 to 100, more preferably 0 to 70, even more preferably 0 to 40,
r preferably 0 to 100, more preferably 0 to 70, even more preferably 0 to 40,
s preferably 0 to 100, more preferably 0 to 70, even more preferably 0 to 40,
q+r+s=1 to 300, more preferably 1 to 100, even more preferred 1 to 50,
In the group -A-(OCH$_2$CH$_2$)$_q$—(OCH$_2$CH(CH$_3$))$_r$—(OCH$_2$CH(C$_2$H$_5$))$_s$-A'- the ethylene oxide and propylene oxide and butylenes oxide units can be positioned in any way, e.g. as statistical copolymer units or as a block copolymer unit.

The polyorganosiloxane compounds of the invention are preferentially produced in a first embodiment via a method, in which first α,ω Si—H functionalized siloxanes of the general structure

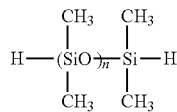

are converted, in the presence of a hydrosilylation catalyst and at temperatures of 50° to 150° C., with 1.0 to 1.5 mol, based upon SiH groups, of an alkenyl-epoxide, which has a terminal olefinic bond, wherein the alkenyl-epoxide contains at least 4 carbon atoms, and may additionally contain a non-cyclical ether group. Vinyl cyclohexene oxide and allylglycide ether are preferably used as epoxy-functional precursors for the production of epoxy functionalized siloxanes. The excess olefinic epoxide is then removed, if necessary.

The bisepoxide is preferably reacted with a mixture of one diamine, for example the preferred diamine of the formula

with R and T as defined above, or a secondary monoamine (that reacts two times to be quaternized).

Optionally in addition a α,ω carboxylic halogen alkyl acid ester may act as an alkylating agent. The α,ω carboxylic halogen alkyl acid ester is preferably of the formula

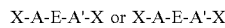

wherein A-E-A' or A'-E-A are as defined above and X is a customary nucleophilic originating group, preferably chloride or bromide, provided that X is bonded to a terminal —CH$_2$-group.

The reaction is preferably carried out in the presence of an organic acid at preferred 40° to 150° C., wherein the molar ratio of tertiary amino groups:Σ (epoxy groups+optional carboxylic haloacid ester groups) is for example ≤1:1, preferred ≤0.98:1, more preferred ≤0.9:1, even more preferred ≤0.7:1, specifically ≤0.5:1, the molar ratio of organic acid:epoxy groups ranges from 3:1 to 1:1, preferred from 2:1 to 1:1, more preferred from 1.5:1 to 1:1, even more preferred from 1.2:1 to 1:1, specifically is 1:1.

This means that i.e. either by reduction of the molar amount on tertiary amine and/or increase of the molar amount of organic acids low viscosity polyorganosiloxane compounds of the invention can be synthesized.

In a preferred variation of the embodiment, the species that contain the various amino groups may be added to the batch optionally together with the carboxylic haloacid ester derivatives, if necessary with the simultaneous addition of equimolar quantities of acid. It is also within the scope of the invention, however, to cause first the epoxy derivatives, the carboxylic haloacid ester derivatives, and the di-tertiary amines to react in the presence of a quantity of acid that is equivalent to that of the epoxy groups, and then, if necessary, to add alkylene oxide derivatives that contain primary or secondary amino groups, if necessary with the addition of acids to the point of equivalence with the amino groups.

It is likewise possible to bring the carboxylic haloacid ester derivatives and the di-tertiary amines to react, forming hydrophilic blocks, and afterwards to add the epoxy derivatives, if necessary adding alkylene oxide derivatives that contain primary or secondary amino groups, in the presence of a quantity of acid that is equivalent to that of the epoxy groups to the reaction mixture.

It is preferred to use biscarboxylic haloacid esters of polyalkylenoxides such as alpha, omega bis-chloroacetic esters of polyethylene oxides, alpha, omega diamino terminated polyalkylene oxides (Jeffamine®) and alpha, omega diepoxy terminated polyalkylene oxides such as DER®, e.g. 632 or 636, as precursors for the polyalkylene oxide moiety in the siloxane copolymers.

It is further within the scope of the invention to cause several siloxane components of various chain lengths to react, while maintaining the desired overall stoichiometry. From this, it follows, e.g., the possibility of creating a desired siloxane chain length by using a single siloxane component or by the purposeful mixture of several siloxane components. Analogously, it is possible to prepare an advantageous average alkylene oxide block length in the form of a monomodal, bimodal, or polymodal dispersion. Further, a desired share of alkylene oxides can be distributed variably between the carboxylic haloacid ester components and the amino components. Parent materials for the production of the preferred α,ω carboxylic haloacid esters, preferably of the formula X-A-E-A'-X or X-A-E-A'-X wherein X is preferably chlorine, bromine,
are expediently low-molecular, oligomeric and polymeric alkylene oxides of the general composition $H(OCH_2CH_2)_q$ $(OCH_2CH(CH_3))_r$—$(OCH_2CH(C_2H_5))_s$ OH wherein q, r and s have the meanings indicated above. Preferred representatives are diethylene glycol, triethylene glycol, tetraethylene glycol, the oligoethylene glycols having molar weights of 300 to 1,000 g/mol, especially approximately 400, approximately 600, and approximately 800, dipropylene glycol, tripropylene glycol, tetraproylene glycol, polypropylene glycols having molar weights of 300 to 3,000 g/mol, especially approximately 300, approximately 600 and approximately 2000 and poly(ethylene-propylene) glycol copolymers having molar weights of 300 to 3,000 g/mol. The esterification is accomplished via known methods. For descriptions of said methods please refer to WO 02/10257, example 11a.

Preferred alkylene oxide derivatives used in accordance with the invention are commercially available under the name Jeffamine® (Huntsman Corp.).

The quaternization and alkylation reactions are preferably run in polar organic solvents.

Suitable solvents are, for example organic solvents and water, including in particular mixtures of organic solvents and water, preferably polar organic solvents and water. Polar organic solvents include generally those comprising at least one heteroatome, like in particular oxygen, e.g., alcohols, especially methanol, ethanol, i-propanol and n-butanol; glycols, such as ethylene glycol, diethylene glycol, triethylene glycol, their methyl-, ethyl- and butyl ethers, 1,2-propylene glycol, dipropylene glycol, tripropylene glycol, their methyl-, ethyl- and butyl ethers and 1,3-propylene glycol; ketones, such as acetone and methylethylketone; esters, such as ethylacetate, butylacetate, methoxypropylacetate and 2-ethyl-hexylacetate; ethers, such as tetrahydrofuran; and nitro compounds, such as nitromethane.

It is preferred to run the reactions with a weight ratio of E polymer components:Σ (organic solvents+water) in a weight-range from 100:0 to 20:80, preferably 99.999:0.001 to 20:80, more preferred 95:5 to 20:80, still more preferred 95:5 to 50:50, even more preferred 95:5 to 60:40.

The amount of water in the composition of the reaction ranges in one embodiment from 0.1-0.5 wt. %, in an other embodiment preferably from 0.01-0.1 wt %; in an other embodiment the amount is in the range of 2-10 wt. % and preferably between 0.5 -2 wt. %. In a preferred embodiment of the invention the desired amount of water is added separately. It is also possible to add the desired amount on water i.e. in form of solvent azeotropes or by the amount which is present in commercial grades.

The above described polyorganosiloxane compounds comprising quaternary ammonium functions and ester functions may contain individual molecules which contain quaternary ammonium functions and no ester functions, molecules which contain quaternary ammonium functions and ester functions as well as molecules which contain ester functions and no quaternary ammonium functions.

The above described polyorganosiloxane compounds comprising quaternary ammonium functions and ester functions are to be understood as mixtures of molecules comprising a certain averaged amount and ratio of both moieties.

Another less preferred embodiment of the invention relates to polyorganosiloxane compositions, comprising:
A) at least one polyorganosiloxane compound, comprising
   a) at least one polyorganosiloxane group,
   b) at least one quaternary ammonium group,
   c) at least one terminal ester group, and
B1) at least one polyorganosiloxane compound, comprising at least one terminal ester group, different from compound A).

Component B1) preferably does not comprise quaternary ammonium groups.

Such polyorganosiloxane compositions are physically mixed in order to adjust a desired total quat ($N^+$):ester group ratio and the desired viscosity.

Both compounds are mixed in a ratio such that the mixtures preferably have viscosities at 20° C. and a shear rate of 0.1 $s^{-1}$ of 500 to 100000 mPas, preferred 500 to 70000 mPas, more preferred 500 to 50000 mPa·s, even more preferred 500 to 20000 mPas, specifically 500 to 10000 mPas, more specifically 500 to 5000 mPa·s.

The preferred polyorganosiloxane compounds B) comprising ester functions are α,ω-ester modified derivatives of the structure

M-(K—$S^1$—K)-M having siloxane chain length' in range from n=0 to 1000, preferred 0 to 500, more preferred 0 to 300, even more preferred 0 to 200, specifically 0 to 100.

Alternatively, comb-like derivatives comprising ester function as side groups in a difunctional siloxane unit (OSiMeR* with R*=carbon bound ester group)), and optionally terminal ester moieties ($O_{1/2}SiMe_2R^*$ with R*=carbon bound ester group) of the same chain length range of siloxy units are also preferred. The number of ester-group-containing siloxy units is preferably from 1 to 500, preferred 1 to 250, more preferred 1 to 150, even more preferred 1 to 100, specifically 1 to 50, even more specific 1 to 25.

Preferred monofunctional organic acids yielding the terminal ester groups are preferably the ones forming the above mentioned counter ions. Preferred examples are $C_1$-$C_{30}$ carboxylic acids, for example C2, C3, C8 acids, $C_{10}$-$C_{18}$ carboxylic acids, for example C12, C14, C16 acids, saturated, unsaturated and hydroxyl functionalized C18 acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

In a further preferred embodiment the present invention relates to a polyorganosiloxane compound consisting essentially of:
a) at least one polyorganosiloxane group,
b) at least one quaternary ammonium group, and
c) at least one terminal ester group.
wherein each structural element a), b), and c) is as defined above.

In this context the term "consisting essentially of" means, that the polyorganosiloxane compound consists only or ois formed solely respectively of the monomer compounds that are required to introduce the structural elements a), b), and c) as defined above.

In such polyorganosiloxane compound the molar ratio of the quaternary ammonium groups b) to the terminal ester groups c) is preferably less than 100:15.

In another preferred embodiment said polyorganosiloxane compound further consists essentially of d) at least one polyalkylene oxide group. That is a further monomer is used to introduce the polyalkylene oxide group d).

In another preferred embodiment said polyorganosiloxane compound further consists essentially of where T is selected from the group of divalent hydrocarbon radicals comprising from one to twenty carbon atoms. That is a further monomer is used to introduce the group T.

The preferred viscosity ranges for the different structure classes are explained in the following.

For a polyorganosiloxane compound having only the structural elements:
a) at least one polyorganosiloxane group,
b) at least one quaternary ammonium group,
c2) at least one terminal ester group,
(that is, none of the structural elements c1), c3), d), e) and f) are present. This applies analogously also to the following polyorganosiloxane compounds):
preferred 500 to 100.000
preferred 500 to 70000,
preferred 500 to 50000,
preferred 500 to 20000,
preferred 500 to 10000,
preferred 500 to 5000,
(each value is mPa·s 25° C. measured at 25° C. and a shear rate of 0.1 s$^{-1}$).

For a polyorganosiloxane compound having only the structural elements:
a) at least one polyorganosiloxane group,
b) at least one quaternary ammonium group,
c) at least one terminal group, selected from the groups consisting of:
c1) at least one terminal monofunctional polyorganosiloxane group,
c2) at least one terminal ester group, and
c3) at least one terminal alkyl-terminated polyether group, and
f) polyalkylene oxide groups, selected from polyalkylene oxide groups lateral to the polymer main chain:
preferred 500 to 10000
preferred 500 to 5000 mPa·s 25° C.
(each value is mPa·s 25° C. measured at 25° C. and a shear rate of 0.1 s$^{-1}$).

For a polyorganosiloxane compound having only the structural elements:
a) at least one polyorganosiloxane group,
b) at least one quaternary ammonium group,
c) at least one terminal group, selected from the groups consisting of:
c1) at least one terminal monofunctional polyorganosiloxane group,
c2) at least one terminal ester group, and
c3) at least one terminal alkyl-terminated polyether group, and
f) polyalkylene oxide groups, selected from polyalkylene oxide groups axial in the polymer main chain:
preferred 500 to 50000
preferred 500 to 20000
preferred 500 to 10000
preferred 500 to 5000
(each value is mPa·s 25° C. measured at 25° C. and a shear rate of 0.1 s$^{-1}$).

For a polyorganosiloxane compound having only the structural elements:
a) at least one polyorganosiloxane group,
b) at least one quaternary ammonium group,
c) at least one terminal group, selected from the groups consisting of:
c1) at least one terminal monofunctional polyorganosiloxane group,
c2) at least one terminal ester group, and
c3) at least one terminal alkyl-terminated polyether group, and
e) branching groups, including branched charged groups:
preferred 500 to 70000
preferred 500 to 50000
preferred 500 to 20000
preferred 500 to 10000
preferred 500 to 5000
(each value is mPa·s 25° C. measured at 25° C. and a shear rate of 0.1 s$^{-1}$).

For a polyorganosiloxane compound having only the structural elements:
a) at least one polyorganosiloxane group,
b) at least one quaternary ammonium group,
c) at least one terminal group, selected from the groups consisting of:
c1) at least one terminal monofunctional polyorganosiloxane group,
c2) at least one terminal ester group, and
c3) at least one terminal alkyl-terminated polyether group, and
d) reactive groups:
preferred 500 to 70000
preferred 500 to 50000
preferred 500 to 20000
preferred 500 to 10000
preferred 500 to 5000
(each value is mPa·s 25° C. measured at 25° C. and a shear rate of 0.1 s$^{-1}$).

For a polyorganosiloxane compound having only the structural elements:
a) at least one polyorganosiloxane group,
b) at least one quaternary ammonium group,
c1) at least one terminal monofunctional polyorganosiloxane group:
preferred 500 to 150000
preferred 500 to 100000
preferred 500 to 70000
preferred 500 to 50000
preferred 500 to 20000
preferred 500 to 10000
preferred 500 to 5000
(each value is mPa·s 25° C. measured at 25° C. and a shear rate of 0.1 s$^{-1}$).

For a polyorganosiloxane composition, comprising:
A) at least one polyorganosiloxane compound, comprising
a) at least one polyorganosiloxane group, and
b) at least one quaternary ammonium group,
c) optionally at least one terminal ester group, and
B) at least one polyorganosiloxane compound, which does not have quaternary ammonium groups, and which polyorganosiloxane compound B) comprises at least one terminal ester group:
preferred 500 to 70000
preferred 500 to 50000
preferred 500 to 20000
preferred 500 to 10000
preferred 500 to 5000

(each value is mPa·s 25° C. measured at 25° C. and a shear rate of 0.1 s$^{-1}$).

The invention further relates to the use of the above-described polyorganosiloxane compounds or compositions of polyorganosiloxane compounds in cosmetic formulations for skin and hair care, in polishing agents for treating and coating hard surfaces, in formulations for drying automobiles and other hard surfaces, for example following automatic washing, for finishing textiles and textile fibers, as separate softeners for use after textiles have been washed with non-ionogenic or anionic/non-ionogenic detergent formulations, as softeners in formulations for washing textiles that are based upon non-ionic or anionic/non-ionic surfactants, and as means for preventing or removing wrinkles in textiles.

The invention further relates to the use of the above-described polyorganosiloxane compounds or compositions as wash-resistant, hydrophilic softeners for use in the original finishing of textiles.

The invention further relates to compositions that contain at least one of the polyorganosiloxane compounds or compositions, together with at least one additional component that is commonly used in such a composition.

Below, a number of typical examples of these types of compositions are provided, in which the polyorganosiloxane compounds of the invention may be advantageously used:

Typical adjuvants in these types of compositions are, e.g., those materials described in A. Domsch: Die kosmetischen Praeparate [Cosmetic Preparations] Vol. I and II, 4$^{th}$ Edition, Verl. fuer chem. Industrie [Publishers for the Chemical Industry], U. Ziolkowsky K G, Augsburg, and the International Cosmetic Ingredient Dictionary and Handbook 7$^{th}$ Ed. 1997 by J. A. Wenninger, G. N. McEwen Vol. 1-4 by The Cosmetic, Toiletry and Fragrance Association Washington D.C.

Anionic Shampoo

This formulation example is intended as a basic formulation. Anionic shampoos customarily contain, but are not limited to, the following components:

Alkylsulfates, alkylether sulfates, sodium lauryl sulfate, sodium lauryl ether sulfate, ammonium lauryl sulfate, ammonium lauryl-ether sulfate, TEA-lauryl sulfate, TEA-lauryl-ether sulfate, alkylbenzene sulfonates, α-olefinsulfonates, paraffin sulfonates, sulfosuccinates, N-acyltaurides, sulfate-glycerides, sulfatized alkanolamides, carboxylate salts, N-acyl-amino acid salts, silicones, etc.

| Components | wt-% |
|---|---|
| Ammonium lauryl sulphate | 10.00-30.00 |
| Ammonium lauryl-ether sulphate | 5.00-20.00 |
| Cocamidopropyl betaine | 0.00-15.00 |
| Lauramide DEA | 0.00-5.00 |
| Cocamide Mea | 0.00-5.00 |
| Dimethicone copolyol (dimethylsiloxane glycol copolymer) | 0.00-5.00 |
| Cyclopentasiloxane | 0.00-5.00 |
| Polyorganosiloxane compound or compositions of the invention | 0.50-5.00 |
| Polyquaternium-10 | 0.00-2.00 |
| Preservatives | 0.00-0.50 |
| Fragrance | 0.00-5.00 |
| Deionized water | q.s. 100% |
| Sodium chloride | q.s. |

Non-Ionic Shampoo

This formulation example is intended as a basic formulation. Non-ionic shampoos customarily contain, but are not limited to, the following components:

Monoalkanolamides, monoethanolamides, monoisopropanolamides, polyhydroxy derivatives, sucrose monolaurate, polyglycerine ether, amine oxides, polyethoxylated derivatives, sorbitol derivatives, silicones, etc.

| Components | Wt-% |
|---|---|
| Lauramide DEA | 10.00-30.00 |
| Lauramide oxide | 5.00-20.00 |
| Cocamide Mea | 0.00-5.00 |
| Dimethicone copolyol | 0.00-5.00 |
| Polyorganosiloxane compound or compositions of the invention | 0.50-5.00 |
| Preservatives | 0.00-0.50 |
| Fragrance | 0.00-5.00 |
| Deionized water | q.s. 100% |
| Sodium chloride | q.s. |

Amphoteric Shampoo

This formulation example is intended as a basic formulation. Formulations of this category customarily contain, but are not limited to, the following components:

N-alkyl-iminodipropionates, N-alkyl-iminopropionates, amino acids, amino acid derivatives, amido betaine, imidazolinium derivatives, sulfobetaines, sultaines, betaines, silicones, etc.

| Components | Wt-% |
|---|---|
| PEG-80-sorbitane laurate | 10.00-30.00 |
| Lauroamphoglycinate | 0.00-10.00 |
| Cocamidopropyl-hydroxysultain | 0.00-15.00 |
| PEG-150-distearate | 0.00-5.00 |
| Laurylether-13-carboxylate | 0.00-5.00 |
| Polyorganosiloxane compound or compositions of the invention | 0.50-5.00 |
| Fragrance | 0.00-5.00 |
| Deionized water | q.s. 100% |
| Sodium chloride | q.s. |

Cationic Shampoo

This formulation example is intended only as a basic formulation. Formulations of this category customarily contain, but are not limited to, the following components:

Bis-quaternary ammonium compounds, bis-(trialkylammonium acetyl)diamines, amido amines, ammonium alkylesters, silicones, etc.

| Components | Wt-% |
|---|---|
| Laurylether-13-carboxylate | 10.00-30.00 |
| Isopropylmyristate | 5.00-20.00 |
| Cocamidopropyl-betaine | 0.00-15.00 |
| Lauramide DEA | 0.00-5.00 |
| Cocamide MEA | 0.00-5.00 |
| Polyorganosiloxane compound or composition specified in the invention | 0.50-5.00 |
| Preservatives | 0.00-0.50 |
| Fragrance | 0.00-5.00 |
| Deionized water | q.s. 100% |
| Sodium chloride | q.s. |

Setting or Solidifying Agents

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, etc.

| Components | Wt-% |
|---|---|
| Ceteareth-20 | 0.10-10.00 |
| Steareth-20 | 0.10-10.00 |
| Stearyl alcohol | 0.10-10.00 |
| Stearamidopropyl-dimethylamine | 0.00-10.00 |
| Dicetyldimonium-chloride | 0.00-10.00 |
| Polyorganosiloxane compound or composition of the invention | 0.50-5.00 |
| Cyclopentasiloxane | 0.00-5.00 |
| Dimethicone | 0.00-5.00 |
| Preservatives | 0.00-0.50 |
| Fragrance | 0.00-5.00 |
| Deionized water | q.s. 100% |

"Clear Rinse-Off" Setting or Solidifying Agents

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, etc.

| Components | Wt-% |
|---|---|
| Glycerin | 0.10-10.00 |
| Cetrimonium chloride | 0.00-10.00 |
| Polyorganosiloxane compound or composition of the invention | 0.50-5.00 |
| Hydroxyethyl cellulose | 0.00-5.00 |
| Preservatives | 0.00-0.50 |
| Fragrance | 0.00-5.00 |
| Deionized water | q.s. 100% |

Foam Setting or Solidifying Agents for Hair

This formulation example is intended as a basic formulation. Formulations of this category contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound or composition of the invention | 0.50-5.00 |
| Nonoxynol-15 | 0.00-2.00 |
| Nonoxynol-20 | 0.00-2.00 |
| Fragrance | 0.00-5.00 |
| Aerosol propellants | 0.00-20.00 |
| Preservatives | 0.00-0.50 |
| Deionized water | q.s. 100% |

Pump Spray (Setting or Solidifying Agents) for Hair

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | Wt-% |
|---|---|
| Polyorganosiloxane compound or composition of the invention | 0.50-5.00 |
| Cyclomethicone | 0.00-80.00 |
| Ethanol | 0.00-80.00 |
| Preservatives | 0.00-0.50 |
| Fragrance | 0.00-5.00 |
| Deionized water | q.s. 100% |

Setting or Solidifying Agent Spray for Hair

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound or composition of the invention | 0.50-5.00 |
| Cyclomethicone | 0.00-80.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Gel Setting or Solidifying Agents for Hair

This formulation example is intended as a basic formulation. Formulations of this category customarily contain, but are not limited to, the following components: thickening agents, cellulose derivatives, acrylic acid derivatives, fixative polymers, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffin solvents, etc.

| Components | Wt-% |
|---|---|
| Polyorganosiloxane compound or composition of the invention | 0.50-5.00 |
| Hydroxyethyl cellulose | 0.00-2.00 |
| Fragrance | 0.00-5.00 |
| Preservatives | 0.00-0.50 |
| Citric acid | 0.00-2.00 |
| Deionized water | q.s. 100% |

Rinse off Conditioner

This formulation example is intended as a basic formulation. Formulations of this category customarily contain, but are not limited to, the following components: hydrocarbon based cationic conditioning agents, silicone based cationic conditioning agents, high melting fatty compounds, low melting oil like ester compounds, thickening agents, cellulose derivatives, fixative polymers, ethylene glycols, propylene glycols, glycol esters, glycerin, glycerin esters, monohydric alcohols, polyhydric alcohols, cationic polymers, nonionic and betain co-emulsifiers, silicones, complexing agents, solvents, fragrances, vitamins, solvents, etc.

| Components | Wt-% |
|---|---|
| Polyorganosiloxane compound or composition of the invention | 0.50-10.00 |
| Cetyl Hydroxyethyl cellulose | 0.00-3.00 |
| Cetearyl alcohol | 0.00-3.00 |
| Glyceryl stearate and PEG-100 Stearate | 0.00-3.00 |
| Tetrasodium EDTA | 0.00-1.00 |
| Deionized water | q.s. 100% |

Styling Gel for Hair

This formulation example is intended as a basic formulation. Formulations of this category customarily contain, but are not limited to, the following components:

Fixative polymers, lacquers, acrylic acid derivatives, cellulose derivatives, vinyl derivatives, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | % |
|---|---|
| Polyorganosiloxane compound or composition of the invention | 0.50-5.00 |
| Fixing agents | 0.10-10.00 |
| Hydroxyethyl cellulose | 0.00-2.00 |
| Fragrance | 0.00-5.00 |
| Citric acid | 0.00-2.00 |
| Deionized water | q.s. 100% |

Styling Spray for Hair

This formulation example is intended as a basic formulation. Formulations of this category customarily contain, but are not limited to, the following components:

Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound or composition of the invention | 0.50-5.00 |
| Cyclomethicone | 0.00-80.00 |
| Fixing agents | 0.10-10.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Pump Spray (Styling) for Hair

This formulation example is intended as a basic formulation. Formulations of this category customarily contain, but are not limited to, the following components:

Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound or composition of the invention | 0.50-5.00 |
| Fixing agents | 0.10-10.00 |
| Cyclomethicone | 0.00-80.00 |
| Ethanol | 0.00-50.00 |
| Preservatives | 0.00-0.50 |
| Fragrance | 0.00-5.00 |
| Deionized water | q.s. 100% |

The use of the polyorganosiloxane derivatives specified in the invention for applications in the hair care field produces favorable results with respect to strengthening, shine, fixing (hold), body, volume, moisture regulation, color retention, protection against environmental factors (UV, salt water, etc.), manageability, antistatic properties, ability to dye, etc.

EXAMPLES

The following examples are intended to describe the present invention in greater detail, without limiting its scope.
Evaluation of the Dispersibility:

The test was conducted by the following procedure:

4 g of the polyorganosiloxanes or the polyorganosiloxane compositions were added to 200 g of water and subjected to mixing with an Ultra Turrax (4000 rpm/2 min) at 25° C. for 3 min.

Afterwards the quality of the dispersion was evaluated visually by the rating criterias:

| Rating | material dispersed | stick of lumps to the beaker wall |
|---|---|---|
| Very poor | no | big lumps stick to beaker wall |
| Poor | some material dispersed | big lumps stick to beaker wall |
| Acceptable | material partially dispersed | some small lumps stick to beaker wall |
| Good | material dispersed | minor quantities of small lumps stick to beaker wall |
| Very good | material dispersed | no |

Example 1

Non Inventive

In a 500 ml three-necked flask, equipped with refluxing condenser, thermometer and mechanical stirrer, 150 g (58.7 mmol epoxy groups) of a silicone diepoxide of the structure

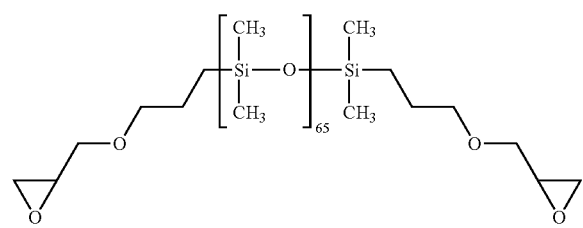

11.76 g (58.7 mmol) lauric acid, 5.06 g N,N,N',N'-tetramethylhexanediamine (58.7 mmol tert. amine), 31.3 g 2-propanol and 10.4 g distilled water are mixed at room temperature. The mixture is heated to reflux for 6 hours. Afterwards, the solvents are removed and the material analyzed by means of NMR and viscometry (see tab. 1). The dispersibility in water as well as the stability of the emulsion is poor.

Example 2

Inventive

In a 500 ml three-necked flask, equipped with refluxing condenser, thermometer and mechanical stirrer, 150 g (58.7 mmol epoxy groups) of a silicone diepoxide of the structure

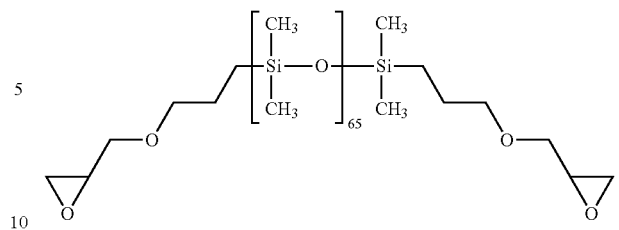

11.76 g (58.7 mmol) lauric acid, 2.53 g N,N,N',N'-tetramethylhexanediamine (29.35 mmol tert. amine), 30.8 g 2-propanol and 10.3 g distilled water are mixed at room temperature. The mixture is heated to reflux for 6 hours. Afterwards, the solvents are removed and the material analyzed by means of NMR and viscometry (see tab. 1). The dispersibility in water as well as the stability of the emulsion is improved and on an acceptable level.

TABLE 1

| expl. # | solids % 120° C./30 min | viscosity mPas 20° C. 0.1 s−1 | ratio $N^+$:ester ** | dispersibility in water* |
|---|---|---|---|---|
| 1 | 98.0 | 112,000 | 100:18.7 | very poor |
| 2 | 98.3 | 8,300 | 100:68.5 | good |

*4 g of polyorganosiloxane material were added to 200 g of water and subjected to mixing with an Ultra Thurrax,
** $^{13}$C-NMR e.g. in $CDCl_3$ 179 ($N^+$) ppm: 174 (ester) ppm.

The data show that in the case of example 1 the non inventive reaction protocol yields a material which contains some ester functions but is too high in viscosity. As a consequence a very poor, uneven, lumpy and sticky dispersion in water is formed. Example 2 shows that reaction protocols according to the invention yield low viscosity materials which can be dispersed easily to small droplets having a sufficient stability.

Example 3

Inventive

The non inventive product of example 1 is mixed with a lauroyl ester modified siloxane of the structure

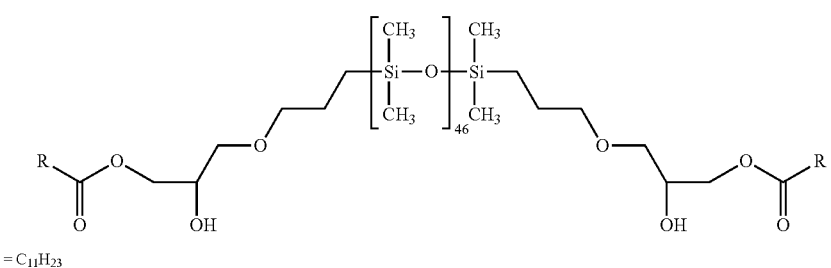

R = $C_{11}H_{23}$ which was synthesized from the corresponding epoxysiloxane, lauric acid and triethylamine (catalyst) in propylene glycol mono methyl ether according to WO 2011/064255.

The blending experiments are summarized in tab. 2.

TABLE 2

| expl. # | ratio expl. 1:lauroyl ester | viscosity mPa · s 20° C. 0.1 s$^{-1}$ | dispersibility in water* |
|---|---|---|---|
| 3.1 | 100:0 | 112,000 | very poor |
| 3.2 | 90:10 | 52,700 | acceptable |
| 3.3 | 75:25 | 20,000 | good |

*4 g of polyorganosiloxane material were added to 200 g of water and subjected to mixing with an Ultra Thurrax.

The data for the examples 3.2 and 3.3 in tab. 2 show that the physical blending of the non inventive material of example 1 with an ester modified siloxane yields mixtures which fall under the invention.

Example 4

Inventive

In a 500 ml three-necked flask, equipped with refluxing condenser, thermometer and mechanical stirrer, 97.4 g (9 mmol epoxy groups) of a silicone diepoxide of the structure

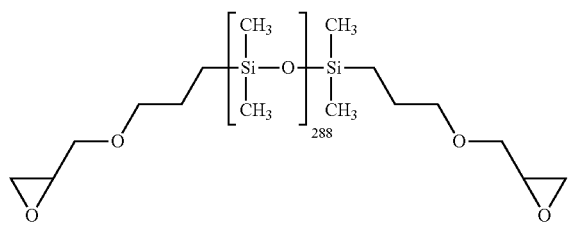

0.36 g (6 mmol) acetic acid, 0.52 g N,N,N',N'-tetramethylhexanediamine (6 mmol tert. amine), 96.5 g methoxy propanol and 1.97 g distilled water are mixed at room temperature. The mixture is heated to reflux for 4 hours. Afterwards, 0.18 g (3 mmol) acetic acid is added and the mixture maintained at reflux for additional 4 hours.

The solvents are removed. A polymeric material is obtained having a solids content of 95.68% (120° C./30 min) and a viscosity of 4300 mPa·s (20° C., 0.1 s$^{-1}$).

Example 5

Inventive

Conditioning performance was evaluated using a Diastron Combing Force apparatus. Single bleached tresses (4 g) from International Hair Importers were washed with 10% sodium lauryl sulphate solution and dried. The tresses were placed in a controlled humidity chamber at 50% (relative humidity RH) overnight before the baseline measurement of combing force, $F_b$.

The silicone polymer was dissolved in isopropanol to obtain solutions of 0.014 wt-% and 0.07 wt-%. About 2.8 g of isopropanol solution was distributed evenly on the hair tress with a pipette to obtain 100 ppm and 500 ppm silicone polymer on the hair, respectively. After overnight drying in a 50° C. oven, the tresses were placed in the controlled humidity chamber at 50% RH before the treated tress measurement of combing force, $F_t$. The dry combing force reduction corresponded to the value of $(F_b-F_t)\cdot 100/F_t$.

The results are summarized in tab. 3.

TABLE 3

| Concentration | | 500 ppm | 100 ppm |
|---|---|---|---|
| Silicone example 4 | $(F_b - F_t) \cdot 100/F_t$ | 58.8 | 36.9 |
| Commercially avalaible product )$^3$ | $(F_b - F_t) \cdot 100/F_t$ | 62.2 | -2.2 |

)$^3$ polyaminopropylmethylsiloxane

Tab. 3 shows that the inventive polyorganosiloxane provide a much better dry combing force reduction at low concentrations in the composition for hair treatment.

Example 6

In a 500 ml three-necked flask, equipped with refluxing condenser, thermometer and mechanical stirrer, 122.6 g (48 mmol epoxy groups) of a silicone diepoxide of the structure

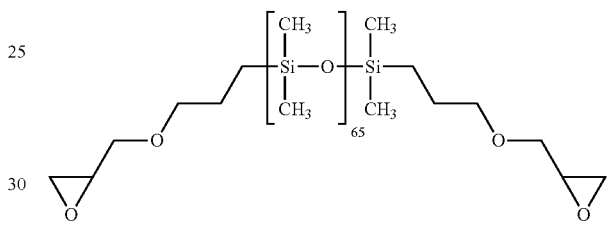

and 2.88 g (9.6 mmol NH functions) of an amine of the structure H$_2$N[CH(CH$_3$)CH$_2$O)$_1$(CH$_2$CH$_2$O)$_9$]CH$_3$ (Jeffamine M600, Huntsman) are mixed at room temperature and heated to 120° C. for 4 hrs. 1.23 g (4.8 mmol CH$_2$Cl) of an ester of the structure ClCH$_2$C(O)O(CH$_2$CH$_2$O)$_3$CH$_3$, synthesized in analogy to U.S. Pat. No. 8,076,442, example 5a, are added. The mixture is kept at 120° C. for additional 4 hrs. The mixture is cooled to 100° C. A mixture consisting of 7.68 g (38.4 mmol) lauric acid, 3.31 g N,N,N',N'-tetramethylhexanediamine (38.4 mmol tert. amine), 16.2 g propylene glycol monomethyl ether and 8.1 g distilled water is added and the reaction continued at 100° C. for 6 hrs. Afterwards, the solvents are removed and the material analyzed by means of NMR and viscometry (see tab. 4).

Example 7

In a 500 ml three-necked flask, equipped with refluxing condenser, thermometer and mechanical stirrer, 122.6 g (48 mmol epoxy groups) of a silicone diepoxide of the structure

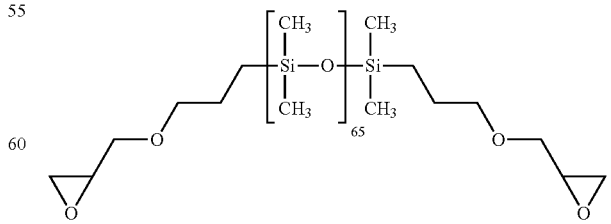

and 2.88 g (9.6 mmol NH functions) of an amine of the structure H$_2$N[CH(CH$_3$)CH$_2$O)$_1$(CH$_2$CH$_2$O)$_9$]CH$_3$ (Jeffamine M600, Huntsman) are mixed at room temperature and heated to 120° C. for 4 hrs. 1.23 g (4.8 mmol CH$_2$Cl) of an ester of the structure ClCH$_2$C(O)O(CH$_2$CH$_2$O)$_3$CH$_3$, synthesized in analogy to U.S. Pat. No. 8,076,442, example 5a, are added. The mixture is kept at 120° C. for additional 4 hrs. The mixture is cooled to 100° C. A mixture consisting of 7.68 g (38.4 mmol) lauric acid, 1.65 g N,N,N',N'-tetramethylhexanediamine (19.2 mmol tert. amine), 16 g propylene glycol monomethyl ether and 8 g distilled water is added and the reaction continued at 100° C. for 6 hrs. Afterwards, the solvents are removed and the material analyzed by means of NMR and viscometry (see tab. 4).

Example 8

In a 500 ml three-necked flask, equipped with refluxing condenser, thermometer and mechanical stirrer, 122.6 g (48 mmol epoxy groups) of a silicone diepoxide of the structure

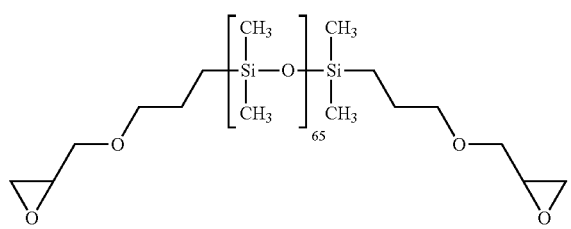

0.78 g (6 mmol CH$_2$Cl) ClCH$_2$C(O)OCH$_2$CH$_2$OCH$_2$CH$_2$OC(O)CH$_2$Cl, 0.64 g (6 mmol CH$_2$Cl) of an ester of the structure

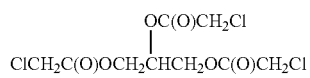

synthesized in analogy to U.S. Pat. No. 7,390,479, example 4b, 9.6 g (48 mmol) lauric acid, 5.17 g N,N,N',N'-tetramethylhexanediamine (60 mmol tert. amine), 16.3 g propylene glycol monomethyl ether and 8.2 g distilled water are mixed at room temperature and heated to reflux for 7 hrs. Afterwards, the solvents are removed and the material analyzed by means of NMR and viscometry (see tab. 4).

Example 9

In a 500 ml three-necked flask, equipped with refluxing condenser, thermometer and mechanical stirrer, 122.6 g (48 mmol epoxy groups) of a silicone diepoxide of the structure

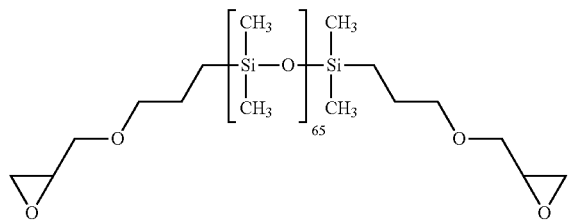

0.78 g (6 mmol CH$_2$Cl) ClCH$_2$C(O)OCH$_2$CH$_2$OCH$_2$CH$_2$OC(O)CH$_2$Cl, 0.64 g (6 mmol CH$_2$Cl) of an ester of the structure

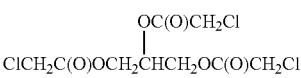

synthesized in analogy to U.S. Pat. No. 7,390,479, example 4b, 9.6 g (48 mmol) lauric acid, 2.59 g N,N,N',N'-tetramethylhexanediamine (30 mmol tert. amine), 16.3 g propylene glycol monomethyl ether and 8.2 g distilled water are mixed at room temperature and heated to reflux for 7 hrs. Afterwards, the solvents are removed and the material analyzed by means of NMR and viscometry (see tab. 4).

Example 10

In a 250 ml three-necked flask, equipped with refluxing condenser, thermometer and mechanical stirrer, 50 g (15.34 mmol epoxy groups) of a silicone diepoxide of the structure

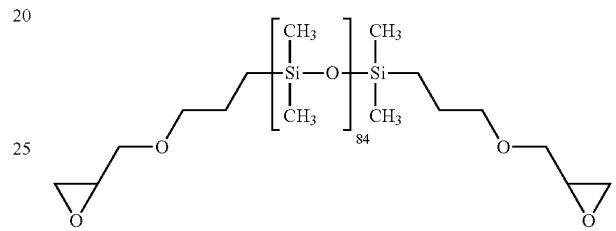

0.22 g (1.7 mmol CH$_2$Cl) ClCH$_2$C(O)OCH$_2$CH$_2$OCH$_2$CH$_2$OC(O)CH$_2$Cl, 0.47 g (1.7 mmol tert. amino functions) of an uretdione derivative of the structure

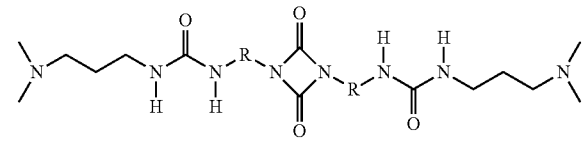

wherein R is a mixture consisting of

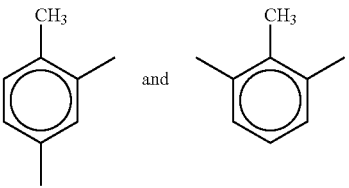

(synthesized from the corresponding toluene diisocyanate dimer and H$_2$NCH$_2$CH$_2$CH$_2$N(CH$_3$)$_2$ in analogy to U.S. Pat. No. 7,863,397, expl. 1a),
3.07 g (15.34 mmol) lauric acid, 1.32 g N,N,N',N'-tetramethylhexanediamine (15.34 mmol tert. amine), 6.48 g propylene glycol monomethyl ether and 3.24 g distilled water are mixed at room temperature and heated to reflux for 6 hrs. Afterwards, the solvents are removed and the material analyzed by means of NMR and viscometry (see tab. 4).

Example 11

In a 250 ml three-necked flask, equipped with refluxing condenser, thermometer and mechanical stirrer, 50 g (15.34 mmol epoxy groups) of a silicone diepoxide of the structure

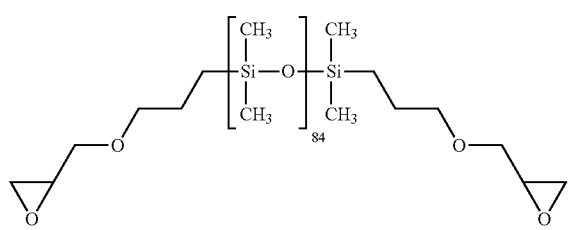

0.22 g (1.7 mmol CH₂Cl) ClCH₂C(O)OCH₂CH₂OCH₂CH₂OC(O)CH₂Cl, 0.47 g (1.7 mmol tert. amino functions) of an uretdione derivative of the structure

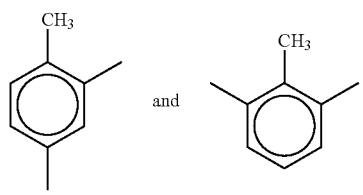

wherein R is a mixture consisting of

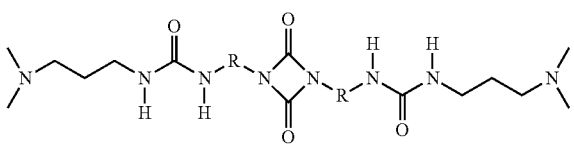

(synthesized from the corresponding toluene diisocyanate dimer and H₂NCH₂CH₂CH₂N(CH₃)₂ in analogy to U.S. Pat. No. 7,863,397, expl. 1a), 3.07 g (15.34 mmol) lauric acid, 0.587 g N,N,N',N'-tetramethylhexanediamine (6.82 mmol tert. amine), 6.38 g propylene glycol monomethyl ether and 3.19 g distilled water are mixed at room temperature and heated to reflux for 6 hrs. Afterwards, the solvents are removed and the material analyzed by means of NMR and viscometry (see tab. 4).

TABLE 4

| example | solids % 120° C./30 min | viscosity mPa · s 20° C., 0.1 s−1 | ratio N⁺:ester ** | dispersibility in water* |
| --- | --- | --- | --- | --- |
| 6 | 97.1 | 13.000 | 100:9.7 | good |
| 7 | 97.2 | 1.400 | 100:51.4 | very good |
| 8 | 97.4 | 94.000 | 100:4.1 | poor |
| 9 | 97.5 | 4.600 | 100:22.6 | very good |
| 10 | 98.3 | 109.000 | 100:15.0 | poor |
| 11 | 98.4 | 9.400 | 100:27.7 | good |

*4 g of polyorganosiloxane material were added to 200 g of water and subjected to mixing with an Ultra Thurrax.
**($^{13}$C-NMR) e.g. in CDCl₃ 179 ppm (N⁺):174 (ester) ppm The data for the examples 7, 9, and 11 shows that compounds having a low ratio N⁺:ester (high amount of ester groups) yield lower viscous materials compared to the compounds having a high ratio N⁺:ester (low amount of ester groups). The preferred materials contain higher portions of ester groups. They can be better dispersed than the materials containing lower portions of ester groups.

Example 12

Polyorganosiloxane Composition

The product of example 10 is mixed with a lauroyl ester modified siloxane of the structure

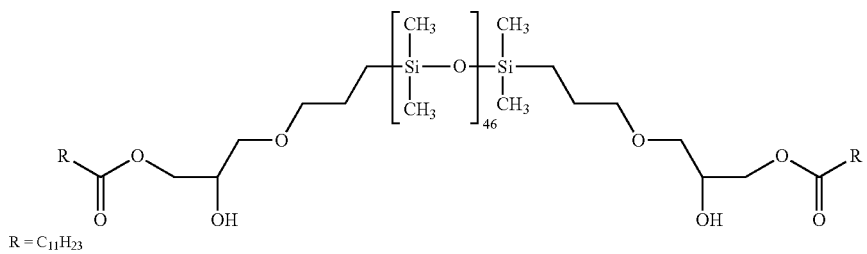

which was synthesized from the corresponding epoxysiloxane, lauric acid and triethylamine (catalyst) in propylene glycol monomethyl ether according to WO 2011/064255.

The blending experiments are summarized in tab. 5.

TABLE 5

| examples | weight ratio example 10:lauryl ester | viscosity mPa · s 20° C., 0.1 s−1 | dispersibility in water* |
| --- | --- | --- | --- |
| 12.1 | 100:0 | 109.000 | poor |
| 12.2 | 90:10 | 45.400 | acceptable |
| 12.3 | 75:25 | 14.200 | good |
| 12.4 | 50:50 | 2.900 | very good |
| 12.5 | 25:75 | 650 | very good |
| 12.6 | 0:100 | 270 | poor |

*4 g of polyorganosiloxane material were added to 200 g of water and subjected to mixing with an Ultra Thurrax.

The data for the examples 12.2 to 12.5 in tab. 5 show that the physical blending of the material of example 10 with lower ester group content with an ester modified siloxane yields mixtures which can be dispersed in water.

Examples 13 to 16

These examples show the effect of the terminal monofunctional polyorganosiloxane group.

Example 13

In a 500 ml three-necked flask, equipped with refluxing condenser, thermometer and mechanical stirrer, 257.1 g (23.7 mmol epoxy groups) of a silicone diepoxide of the structure

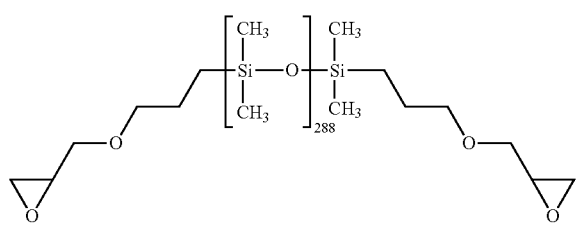

0.34 g (2.64 mmol CH$_2$Cl) ClCH$_2$C(O)OCH$_2$CH$_2$OCH$_2$CH$_2$OC(O)CH$_2$Cl, 4.75 g (23.76 mmol) lauric acid, 2.27 g (26.4 mmol tert. amine) N,N,N',N'-tetramethylhexanediamine, 31 g propylene glycol monomethyl ether and 15.5 g distilled water are mixed at room temperature and heated to reflux for 16 hrs. Afterwards, the solvents are removed and the material analyzed by means of viscometry (see tab. 6).

Example 14

In a 500 ml three-necked flask, equipped with refluxing condenser, thermometer and mechanical stirrer, 200 g (18.48 mmol epoxy groups) of a silicone diepoxide of the structure

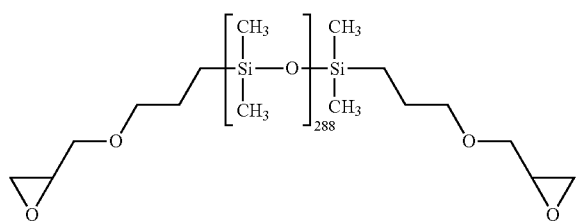

111.4 g (5.28 mmol total epoxy groups) of a silicone monoepoxide of the structure

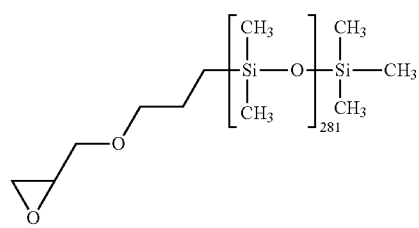

which contains approx. 50% target silicone monoepoxide, 25% silicone diepoxide and 25% non functional PDMS of the averaged structure

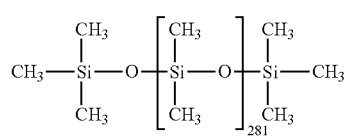

0.34 g (2.64 mmol CH$_2$Cl) ClCH$_2$C(O)OCH$_2$CH$_2$OCH$_2$CH$_2$OC(O)CH$_2$Cl, 4.75 g (23.76 mmol) lauric acid, 2.27 g (26.4 mmol tert. amine) N,N,N',N'-tetramethylhexanediamine, 37.5 g propylene glycol monomethyl ether and 18.75 g distilled water are mixed at room temperature and heated to reflux for 16 hrs. Afterwards, the solvents are removed and the material analyzed by means of viscometry (see tab. 6).

Example 15

In a 500 ml three-necked flask, equipped with refluxing condenser, thermometer and mechanical stirrer, 111.5 g (71.28 mmol epoxy groups) of a silicone diepoxide of the structure

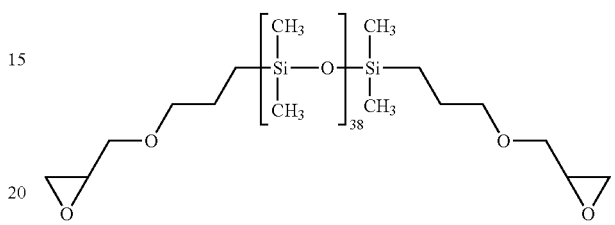

1.03 g (7.92 mmol CH$_2$Cl) ClCH$_2$C(O)OCH$_2$CH$_2$OCH$_2$CH$_2$OC(O)CH$_2$Cl, 14.26 g (71.28 mmol) lauric acid, 6.82 g (79.2 mmol tert. amine) N,N,N',N'-tetramethylhexanediamine, 23.58 g propylene glycol monomethyl ether and 7.8 g distilled water are mixed at room temperature and heated to reflux for 12 hrs. Afterwards, the solvents are removed and the material analyzed by means of viscometry (see tab. 6).

Example 16

In a 500 ml three-necked flask, equipped with refluxing condenser, thermometer and mechanical stirrer, 28.9 g (18.48 mmol epoxy groups) of a silicone diepoxide of the structure

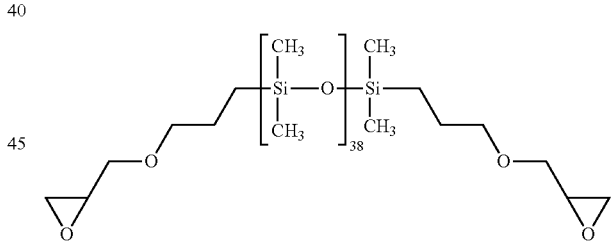

111.4 g (5.28 mmol total epoxy groups) of a silicone monoepoxide of the structure

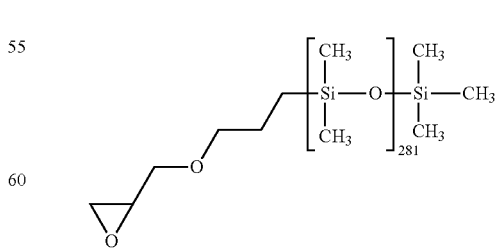

which contains approx. 50% target silicone monoepoxide, 25% siliocone diepoxide and 25% non functional PDMS of the averaged structure

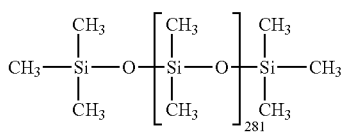

0.34 g (2.64 mmol CH$_2$Cl) ClCH$_2$C(O)OCH$_2$CH$_2$OCH$_2$CH$_2$OC(O)CH$_2$Cl, 4.75 g (23.76 mmol) lauric acid, 2.27 g (26.4 mmol tert. amine) N,N,N',N'-tetramethylhexanediamine, 26.05 g propylene glycol monomethyl ether and 8.7 g distilled water are mixed at room temperature and heated to reflux for 16 hrs. Afterwards, the solvents are removed and the material analyzed by means of viscometry (see tab. 6).

TABLE 6

| Examples | solids % 120° C./30 min | viscosity mPa · s 20° C., 0.1 s$^{-1}$ | dispersibility in water* |
|---|---|---|---|
| 13 | 98.3 | 300.000 | very poor |
| 14 | 97.9 | 105.000 | acceptable |
| 15 | 96.8 | 39.200 | acceptable |
| 16 | 96.9 | 13.600 | good |

*4 g of polyorganosiloxane material were added to 200 g of water and subjected to mixing with an Ultra Thurrax.

The data show that compounds having terminal monofunctional polyorganosiloxane groups yield lower viscous materials.

The invention claimed is:

1. A polyorganosiloxane compound comprising:
   a) at least one polyorganosiloxane group,
   b) at least one quaternary ammonium group, and
   c) at least one terminal group, selected from the groups consisting of:
      c1) at least one terminal monofunctional polyorganosiloxane group,
      c2) at least one terminal ester group, and
      c3) at least one terminal alkyl-terminated polyether group;
   wherein the polyorganosiloxane compound contains at least one terminal ester group c2); and
   wherein the molar ratio of the quaternary ammonium groups b) and the terminal ester groups c2) is less than 100:15.

2. A polyorganosiloxane compound according to claim 1, further comprising at least one functional group selected from the group consisting of:
   d) reactive groups,
   e) branching groups, and
   f) polyalkylene oxide groups.

3. A polyorganosiloxane compound according to claim 2, wherein the polyalkylene oxide group is an axial group in the polymer main chain of the general formula:

-A-E-A'- wherein A and A' each are independently selected from the group consisting of a single bond and a divalent organic group having up to 10 carbon atoms and optionally having one or more hetero atoms, and
   E is a polyalkylene oxide group of the general formula:

—[CH$_2$CH$_2$O]$_q$—[CH$_2$CH(CH$_3$)O]$_r$—[CH$_2$CH(C$_2$H$_5$)O]$_s$— with
   q=0 to 200,
   r=0 to 200,
   s=0 to 200
   and q+r+s=1 to 600.

4. A polyorganosiloxane compound according to claim 3, wherein A and A' are independently selected from the group consisting of
   —CH$_2$CH(CH$_3$)—
   —[CH$_2$CH$_2$O]$_q$—[CH$_2$CH(CH$_3$)O]$_r$—[CH$_2$CH(C$_2$H$_5$)O]$_s$—
   —CH$_2$C(O)O—, —CH$_2$CH$_2$C(O)O—, —CH$_2$CH$_2$CH$_2$C(O)O—, —OC(O)CH$_2$—, —OC(O)CH$_2$CH$_2$—, —OC(O)CH$_2$CH$_2$CH$_2$—, —CH$_2$C(O)—, —CH$_2$CH$_2$C(O)—, —CH$_2$CH$_2$CH$_2$C(O)—, —C(O)CH$_2$—, —C(O)CH$_2$CH$_2$—, —C(O)CH$_2$CH$_2$CH$_2$—,
   —CH$_2$CH(OH)CH$_2$—, —O—CH$_2$CH(OH)CH$_2$—, —CH$_2$CH(OH)CH$_2$—O—,
   —[CH$_2$CH$_2$O]$_q$—[CH$_2$CH(CH$_3$)O]$_r$—[CH$_2$CH(C$_2$H$_5$)O]$_s$—

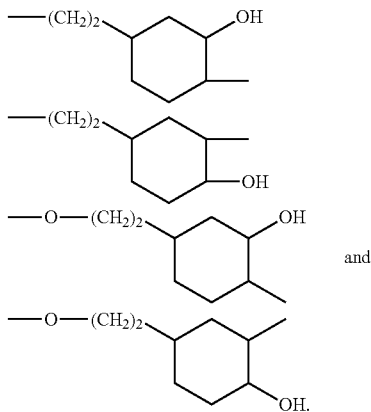

and

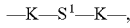

5. A polyorganosiloxane compound according to claim 1, comprising at least one polyorganosiloxane group of the general formula:

—K—S$^1$—K—, with

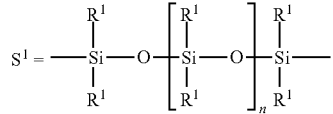

wherein R$^1$=C$_1$-C$_{22}$-alkyl, C$_1$-C$_{22}$-fluoralkyl or aryl,
n=0 to 1000, and these can be identical or different if several S$^1$ Groups are present in the polyorganosiloxane compound,
K=is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above, whereby the residues K can be identical or different from each other.

6. A polyorganosiloxane compound according to claim 1, comprising at least one repeating unit comprising at least one quaternary ammonium group selected from the group consisting of:

—N$^+$R$_2$—,

—N$^+$R$_2$-T-N$^+$R$_2$—, a saturated or unsaturated mono or diquaternary heterocycle of the formulae

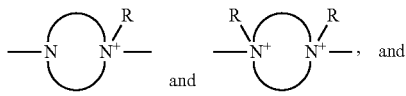
and an aromatic ammonium heterocycle of the formula

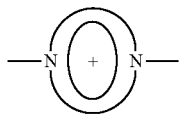

wherein R is selected from the group consisting of monovalent organic groups having up to 22 carbon atoms and optionally one or more heteroatoms, and wherein the free valencies at the nitrogen atoms are bound to carbon atoms, and T is a divalent organic group having up to 20 carbon atoms and one or more hetero atoms.

7. A polyorganosiloxane compound according to claim 1, wherein the terminal monofunctional polyorganosiloxane group is a group of the general formula:

—K—S², wherein K is a bivalent or trivalent straight chain, cyclic and/or branched $C_2$-$C_{40}$ hydrocarbon residue which is optionally interrupted by —O—, —NH—, trivalent N, —NR¹—, —C(O)—, —C(S)—, and optionally substituted with —OH, wherein R¹ is $C_1$-$C_{22}$-alkyl, $C_1$-$C_{22}$-fluoralkyl or aryl, whereby the residues K can be identical or different from each other, and S² is a monofunctional polyorganosiloxanyl group.

8. A polyorganosiloxane compound according to claim 7, wherein the monofunctional polyorganosiloxane group is selected from the group consisting of:

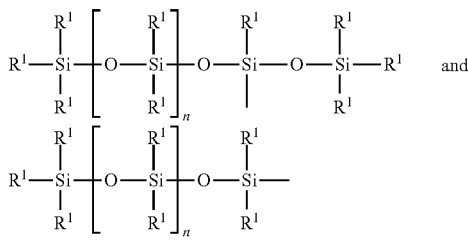

wherein R¹ is $C_1$-$C_{22}$-alkyl, $C_1$-$C_{22}$-fluoralkyl or aryl which are identical or different and n=0 to 1000.

9. A polyorganosiloxane compound according to claim 1, wherein the terminal alkyl-terminated polyether group c3) is a group of the general formula:

-A-E-R⁴ wherein A is selected from a single bond or a divalent organic group having up to 10 carbon atoms and optionally having one or more hetero atoms, and
E is a polyalkylene oxide group of the general formulae:

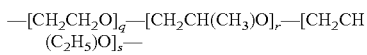

with
q=0 to 200,
r=0 to 200,
s=0 to 200
and q+r+s=1 to 600, and
R⁴ is an alkyl group with up to 6 carbon atoms.

10. A polyorganosiloxane compound according to claim 1, wherein the terminal ester groups are selected from the group consisting of:
—OC(O)—Z
—OS(O)₂—Z
—OS(O₂)O—Z
—OP(O)(O—Z)OH and
—OP(O)(O—Z)₂ wherein Z is selected from monovalent organic residues having up to 40 carbon atoms, optionally comprising one or more hetero atoms.

11. A polyorganosiloxane compound according to claim of the general formula (I):

$$M-Y-[-(N^+R_2-T-N^+R_2)-Y-]_m-M \quad (I),$$

or $$M-Y-[-(N^+R_2)-Y-]_m-M \quad (II)$$

or $$M-Y-[-N^+R_2-Y-]_m-[-(NR^2-A-E-A'-NR^2)-Y-]_k-M \quad (II')$$

wherein:
m is >0,
k is 0 or an average value of >0 to 50,
h is 0 to 100,
R is selected from monovalent organic groups having up to 22 carbon atoms and optionally one or more heteroatoms,
M represents a terminal group c), selected from the groups consisting of:
c1) at least one terminal monofunctional polyorganosiloxane group,
c2) at least one terminal ester group, and
c3) at least one terminal alkyl-terminated polyether group,
wherein in the moiety: -A-E-A'-
A and A' each are independently selected from the group consisting of a single bond and a divalent organic group having up to 10 carbon atoms and optionally having one or more hetero atoms, and
E is a poly-alkylene oxide group of the general formula:

—[CH₂CH₂O]$_q$—[CH₂CH(CH₃)O]$_r$—[CH₂CH(C₂H₅)O]$_s$— with
q=0 to 200,
r=0 to 200,
s=0 to 200
and q+r+s=1 to 600,
R² is selected from hydrogen or R,
Y is T, a group of the formulae:

—K—S—K— and -A-E-A'- or -A'-E-A-, each as defined above, with the proviso that at least one Y is a group of the formula

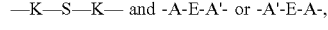—K—S—K— with S=

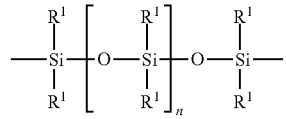

wherein R¹=$C_1$-$C_{22}$-alkyl, $C_1$-$C_{22}$-fluoralkyl or aryl, n=0 to 1000, and these can be identical or different if several S Groups are present in the polyorganosiloxane compound, K=is a bivalent or trivalent straight chain, cyclic and/or branched $C_2$-$C_{40}$ hydrocarbon residue which is optionally interrupted by —O—, —NH—, trivalent N, —NR$^1$—, —C(O)—, —C(S)—, and optionally substituted with —OH, wherein R$^1$=$C_1$-$C_{22}$-alkyl, $C_1$-$C_{22}$-fluoralkyl or aryl, whereby the residues K can be identical or different from each other and T is selected from a divalent organic group having up to 20 carbon atoms and one or inure hetero atoms, X is least one functional group selected from the group consisting of:
d) reactive groups,
e) branching groups and
f) polyalkylene oxide groups, wherein the repeating units having the indices m, k and h, may be arranged in any order.

12. A polyorganosiloxane compound according to claim 11, herein the molar ratio of the repeating group —K—S—K— and the repeating group -A-E-A'- or -A'-E-A- is between 100:1 and 1:100.

13. A polyorganosiloxane compound according to claim 11, wherein the molar ratio of the repeating group —K—S—K— and the group X is between 100:1 and 1:100.

14. A polyorganosiloxane composition comprising:
A) at least one polyorganosiloxane compound, comprising
  a) at least one polyorganosiloxane group,
  b) at least one quaternary ammonium group, and
  c) at least one terminal ester group; and
B) at least one polyorganosiloxane compound, which does not have quaternary ammonium groups, and which polyorganosiloxane compound B) comprises at least one terminal ester group;
wherein in compound A) the molar ratio of the quaternary ammonium groups b) and the terminal ester groups c) is less than 100:10.

15. A polyorganosiloxane composition according to claim 14 wherein the wherein the weight ratio of compound A) to compound B) is less than 90:10.

16. The polyorganosiloxane compound according to claim 1, having a viscosity at 20 and a shear rate of 0.1 s below 200.000 mPa·s.

17. An aqueous emulsions comprising at least one polyorganosiloxane compound as defined in claim 1.

18. A method of surface treatment, comprising the step of applying the polyorganosiloxane compound as defined in claim 1, to the surface of a substrate.

19. The method of claim 18 wherein the polyorganosiloxane compound is present in one of a following compositions or formulations which respectively are applied: cosmetic formulations for skin and hair care, selected front Rinse-oil and Leave-on conditioners, shampoos, styling gels, sprays, and pump sprays; formulations for polishing for the treatment and outfitting of hard surfaces: formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

* * * * *